United States Patent
Woo et al.

(10) Patent No.: US 11,298,178 B2
(45) Date of Patent: *Apr. 12, 2022

(54) MONITORING AND CONTROLLING ENERGY DELIVERY OF AN ELECTROSURGICAL DEVICE

(71) Applicant: Baylis Medical Company Inc., Montreal (CA)

(72) Inventors: Jason Woo, Mississaugua (CA); Taras Juzkiw, Mississauga (CA); Jonathan Dandy, Beaverton, OR (US)

(73) Assignee: Baylis Medical Company Inc., Mississauga (CA)

( * ) Notice: Subject to any disclaimer, the term of this patent is extended or adjusted under 35 U.S.C. 154(b) by 434 days.

This patent is subject to a terminal disclaimer.

(21) Appl. No.: 16/364,952

(22) Filed: Mar. 26, 2019

(65) Prior Publication Data
US 2019/0216528 A1  Jul. 18, 2019

Related U.S. Application Data

(63) Continuation of application No. 14/923,059, filed on Oct. 26, 2015, now Pat. No. 10,271,894, which is a
(Continued)

(51) Int. Cl.
*A61B 18/14* (2006.01)
*A61B 18/12* (2006.01)
(Continued)

(52) U.S. Cl.
CPC .......... *A61B 18/1233* (2013.01); *A61B 46/10* (2016.02); *A61B 90/04* (2016.02);
(Continued)

(58) Field of Classification Search
CPC ..... A61B 18/1233; A61B 18/14; A61B 18/16; A61B 2017/00119; A61B 2018/00577; A61B 2018/00642; A61B 2018/00666; A61B 2018/00898; A61B 2018/00601; A61B 2018/00678; A61B 2018/00702; A61B 2018/0072; A61B 2018/00827; A61B 2018/00845; A61B 2018/00869;
(Continued)

(56) References Cited

U.S. PATENT DOCUMENTS 5,300,068 A * 4/1994 Rosar ................ A61B 18/1492
606/32
5,372,596 A * 12/1994 Klicek .................. A61B 18/12
606/34
(Continued)

*Primary Examiner* — Michael F Peffley
*Assistant Examiner* — Amanda L Zink
(74) *Attorney, Agent, or Firm* — Samuel Tekie; Glenn Arnold; Vincent Man

(57) ABSTRACT

A method is disclosed for delivering energy to a region of tissue within a patient's body using a medical treatment system. The medical treatment system comprises an energy delivery device coupled to an energy source and the method includes steps of delivering energy, measuring an energy delivery parameter, determining distance of the energy delivery device from a conductive object and optionally adjusting a position of the energy delivery device based on the determined distance.

27 Claims, 13 Drawing Sheets

Related U.S. Application Data continuation-in-part of application No. 13/410,868, filed on Mar. 2, 2012, now Pat. No. 9,168,085, which is a continuation-in-part of application No. 13/286,041, filed on Oct. 31, 2011, now Pat. No. 8,623,005, which is a continuation-in-part of application No. 11/905,448, filed on Oct. 1, 2007, now Pat. No. 8,048,071.

(60) Provisional application No. 61/448,578, filed on Mar. 2, 2011, provisional application No. 60/827,466, filed on Sep. 29, 2006.

(51) Int. Cl.
| | | |
|---|---|---|
| *A61B 90/00* | (2016.01) | |
| *A61B 46/10* | (2016.01) | |
| *A61B 18/00* | (2006.01) | |
| *A61B 34/20* | (2016.01) | |
| *A61B 8/12* | (2006.01) | |
| *A61B 18/16* | (2006.01) | |
| *A61B 17/00* | (2006.01) | |

(52) U.S. Cl.
CPC ................ *A61B 8/12* (2013.01); *A61B 18/14* (2013.01); *A61B 18/16* (2013.01); *A61B 90/37* (2016.02); *A61B 2017/00119* (2013.01); *A61B 2018/0072* (2013.01); *A61B 2018/00577* (2013.01); *A61B 2018/00601* (2013.01); *A61B 2018/00642* (2013.01); *A61B 2018/00666* (2013.01); *A61B 2018/00678* (2013.01); *A61B 2018/00702* (2013.01); *A61B 2018/00827* (2013.01); *A61B 2018/00845* (2013.01); *A61B 2018/00869* (2013.01); *A61B 2018/00875* (2013.01); *A61B 2018/00886* (2013.01); *A61B 2018/00892* (2013.01); *A61B 2018/00898* (2013.01); *A61B 2018/1213* (2013.01); *A61B 2034/2059* (2016.02); *A61B 2090/061* (2016.02)

(58) Field of Classification Search
CPC .......... A61B 2018/00875; A61B 2018/00886; A61B 2018/00892; A61B 2018/1213; A61B 2034/2059; A61B 2090/061; A61B 46/10; A61B 8/12; A61B 90/04; A61B 90/37

See application file for complete search history.

(56) References Cited

U.S. PATENT DOCUMENTS

| | | | | |
|---|---|---|---|---|
| 5,540,681 | A | * | 7/1996 | Strul .................. A61B 18/1206 606/1 |
| 5,720,744 | A | * | 2/1998 | Eggleston .......... A61B 18/1206 606/38 |
| 2004/0030328 | A1 | * | 2/2004 | Eggers ............... A61B 18/1206 606/34 |
| 2005/0085806 | A1 | * | 4/2005 | Auge .................... A61B 18/14 606/32 |
| 2005/0149012 | A1 | * | 7/2005 | Penny ................. A61B 18/042 606/41 |
| 2005/0203504 | A1 | * | 9/2005 | Wham ............... A61B 18/1206 606/34 |
| 2006/0106375 | A1 | * | 5/2006 | Werneth ............. A61B 18/1492 606/32 |

\* cited by examiner

MONITORING AND CONTROLLING ENERGY DELIVERY OF AN ELECTROSURGICAL DEVICE

CROSS-REFERENCES TO RELATED APPLICATIONS

This application is a continuation of U.S. application Ser. No. 14/923,059, filed on Oct. 26, 2015, now U.S. Pat. No. 10,271,894, which is a continuation-in-part of U.S. application Ser. No. 13/410,868, filed on Mar. 2, 2012, now U.S. Pat. No. 9,168,085, which is a continuation-in-part of U.S. application Ser. No. 13/286,041, filed on Oct. 31, 2011, now U.S. Pat. No. 8,623,005, which is a continuation-in-part of U.S. application Ser. No. 11/905,448, filed on Oct. 1, 2007, now U.S. Pat. No. 8,048,071.

U.S. application Ser. No. 13/410,868 and U.S. application Ser. No. 13/286,041, further claim the benefit of U.S. provisional application No. 61/448,578, filed on 2 Mar. 2011. U.S. patent application Ser. No. 11/905,448 further claims the benefit of U.S. provisional patent application No. 60/827,466 filed on 29 Sep. 2006. All of these US patent applications and provisional patent applications are hereby incorporated by reference in their entirety.

TECHNICAL FIELD

The disclosure relates to systems and methods for monitoring and controlling energy delivery of an electrosurgical device. More specifically, the disclosure relates to systems and methods for monitoring and controlling delivery of energy to a region of tissue within a patient's body, using an electrosurgical device.

BACKGROUND OF THE ART

U.S. Pat. No. 7,651,492 granted to Wham discloses a system and method for performing electrosurgical procedures. The system includes sensor circuitry adapted to measure impedance and to obtain one or more measured impedance signals. The sensor circuitry is further adapted to generate one or more arc detection signals upon detecting an arcing condition. This is accomplished by passing the measured impedance tissue signal through a high pass filter and then passing the absolute value of the high pass filter through a low pass filter. The resulting filtered signal is the arc detection signal that is scaled and capped. The system disclosed by Wham further includes a controller adapted to generate one or more target control signals as a function of the measured impedance signals and to adjust the output of the electrosurgical generator based on the arc detection signal. Wham discloses detecting arcing by monitoring for rapidly repeating changes in measured signal such as the impedance signal and generating an arc detection signal. Since the system as disclosed by Wham relies on measuring changes in the impedance signal, it will result in the detection of an arcing condition and controlling of the output even if the arcing is insignificant. Furthermore, the system may not respond even if the arcing is significant as long as repeated arcing is not observed. Thus, Wham's system includes several deficiencies with respect to arc detection and energy control.

SUMMARY OF THE DISCLOSURE

In an embodiment of the present invention, a method is disclosed for delivering energy to a region of tissue within a patient's body using a medical treatment system, the medical treatment system comprising a medical device coupled to an energy delivery source, the method comprising the steps of: (1) delivering energy from the medical device; (2) advancing the medical device while delivering energy; (3) measuring an energy delivery parameter while energy is being delivered; (4) detecting if a value of the energy delivery parameter crosses a threshold; (5) if the threshold is crossed thereby indicating proximity of the device to a conductive object, determining the relative distance between the medical device and the conductive object based on one or more detected values of the energy delivery parameter; (6) determining if the distance between the medical device and metal object is decreasing; and (7) upon determining that the distance between the medical device and the conductive object is decreasing, adjusting a position of the medical device and repeating steps (3)-(7) until the medical device is positioned at a desired distance from the conductive object.

As a feature of this broad aspect, the step of adjusting a position of the medical device comprises moving the medical device away from the conductive object until the value of the energy delivery parameter no longer exceeds the threshold.

As another feature of this broad aspect, the conductive object comprises a secondary medical device and wherein the step of adjusting a position of the medical device comprises moving the medical device towards the secondary medical device until the medical device is positioned adjacent the secondary medical device. In one such example the secondary medical device is selected from the group consisting of a medical guidewire and a snare.

As a feature of this broad aspect, the threshold value is equal to a pre-determined value of the energy delivery parameter. As another feature of this broad aspect, the energy delivery parameter is current. In one such example, the threshold value is equal to less than about 1.0 Amps. In one specific example, the threshold value is equal to about 0.3 Amps.

As still another feature of this broad aspect, the threshold value is equal to a base value, wherein the method further comprises a step of determining the base value by measuring the energy delivery parameter upon advancing the medical device to the target site within the patient's body.

In accordance with one embodiment of the present invention, the method further comprises a step of imaging the medical device wherein the steps of advancing the medical device and measuring the base value are performed concurrently with the step of imaging the medical device. In another embodiment, the method further comprises a step of imaging the medical device wherein the step of adjusting a position of the medical device is performed concurrently with the step of imaging the medical device. In some such examples, the step of imaging the medical device is performed using an imaging modality selected from the group consisting of: fluoroscopy, magnetic resonance imaging, computerized tomography scan, electro-anatomical mapping and magnetic positioning system.

As another feature of this broad aspect, the method additionally comprises a step of providing an indication/feedback to the user if the distance between the medical device and the conductive object is determined to be decreasing. As an example of this feature, the indication/feedback is selected from the group consisting of a visual indication, an electrical control signal and an acoustic indication. In a specific example, the acoustic indication is selected from the group consisting of a volume based acoustic indication and a frequency based acoustic indication.

As still another feature of the broad aspect, the step of adjusting a position of the medical device is performed automatically. In one specific example, the step of adjusting a position of the medical device is performed automatically using an automated navigation system. In some such examples, the step of providing an indication/feedback to the user comprises providing an electrical control signal that is receivable by the automated navigation system.

In an alternative embodiment of the present invention, a method is disclosed for delivering energy to a region of tissue within a patient's body using a medical treatment system, the medical treatment system comprising a medical device coupled to an energy delivery source, the method comprising the steps of: (1) delivering energy from the medical device; (2) advancing the medical device while delivering energy; (3) measuring an energy delivery parameter while energy is being delivered; (4) detecting if a value of the energy delivery parameter crosses a threshold; (5) if the threshold is crossed thereby indicating proximity of the device to a conductive object, determining the relative distance between the medical device and the conductive object based on one or more detected values of the energy delivery parameter; (6) determining if the distance between the medical device and metal object is increasing; and (7) upon determining that the distance between the medical device and the conductive object is increasing, adjusting a position of the medical device and repeating steps (3)-(7) until the medical device is positioned at a desired distance from the conductive object.

As another feature of this broad aspect, the method additionally comprises a step of providing an indication/feedback to the user if the distance between the medical device and the conductive object is determined to be increasing.

In accordance with another embodiment of the present invention, a method is disclosed for delivering energy to a region of tissue within a patient's body using a medical treatment system, the medical treatment system comprising a medical device coupled to an energy delivery source, the method comprising: (1) delivering energy from a medical device to material within a patient's body; (2) measuring an energy delivery parameter while the energy is being delivered; (3) detecting at least one error if one or more values of the energy delivery parameter cross a pre-determined threshold; (4) upon detection of at least one error, assessing an extent of the at least one error to determine whether the medical device is sufficiently distanced from a conductive object to allow for safe delivery of the energy to the material within the patient's body; and (5) if the medical device is determined to not be sufficiently distanced from the conductive object, adjusting a position of the medical device and repeating steps (2)-(4) until the medical device is sufficiently distanced from the conductive object.

As a feature of this broad aspect, the energy delivery parameter is selected from the group consisting of: current, voltage, phase, frequency and impedance.

As another feature of this broad aspect, the step of assessing an extent of the at least one error comprises quantifying the number of times the energy delivery parameter crosses the threshold.

As another feature of this broad aspect, the step of determining assessing an extent of the at least one error comprises determining if a collective magnitude of the one or more values of the energy delivery parameter exceeds a sensitivity threshold over a predetermined time period. As an example of this feature, the sensitivity threshold is fixed. As another feature of this example the sensitivity threshold is variable/adjustable;

As another feature of this broad aspect, the step of assessing an extent of the at least one error comprises determining if a duration of time over which the energy delivery parameter exceeds the threshold.

As a feature of this broad aspect, the medical device is selected from the group consisting of a radiofrequency (RF) cutting device and a radiofrequency (RF) ablation device. In one such example, an RF cutting device may have a frequency that is greater than about 500 kHz. In some examples, the RF cutting device may have a radio wave frequency that is between about 30 kHz to about 300 GHz.

In accordance with another embodiment of the present invention, a method is disclosed for delivering energy within a region of tissue within a patient's body using a medical treatment system, the medical treatment system comprising a medical device coupled to an energy delivery source. The method comprises the steps of: (1) delivering energy from the medical device to a material within a patient's body; (2) measuring return current while energy is being delivered; (3) detecting [one or more over-currents] if the return current exceeds a threshold; (4) if the threshold is exceeded, assessing the extent [of the one or more over-currents] by which the return current exceeds the threshold to determine if the medical device is sufficiently distanced from a conductive object; and (5) if the medical device is determined to not be sufficiently distanced from the conductive object, adjusting a position of the medical device and repeating steps (2)-(4) until the medical device is sufficiently distanced from the conductive object.

In accordance with an embodiment of the present invention, a method is disclosed for delivering energy within a region of tissue within a patient's body. The method helps avoid significant arcing while still allowing use of an energy delivery device in the vicinity of an electrically conductive object such as a metallic object. An energy delivery parameter is monitored during the delivery of energy. The value of the energy delivery parameter is compared to a predetermined magnitude threshold to determine if the value exceeds or falls below the predetermined threshold to ascertain if there is significant arcing. The energy delivery is then controlled based on the extent of the arcing observed.

In one broad aspect, embodiments of the present invention comprise a method and medical treatment system for delivering energy to a region of tissue within a patient's body. The medical treatment system comprises an energy delivery device coupled to an energy source. In one particular embodiment, the method comprises the steps of: delivering energy through said energy delivery device; monitoring a current output of said energy delivery device; detecting one or more over-currents if the current output exceeds a predetermined magnitude threshold; determining an extent of the over-currents detected over a predetermined time period; and controlling the delivery of energy based on the extent of the over-currents detected.

In another broad aspect, embodiments of the present invention comprise a method and medical treatment system for delivering energy to a region of tissue within a patient's body. The medical treatment system comprises an energy delivery device coupled to an energy source. In one particular embodiment, the method comprises the steps of: delivering energy through said energy delivery device (which may be positioned within the patient's body); monitoring an energy delivery parameter (for example an electrical parameter) associated with the delivery of energy by the medical treatment system; detecting one or more errors if one or more values of the energy delivery parameter exceed a predetermined magnitude threshold; determining or assessing an extent of the errors detected; and controlling the delivery of energy if the extent of the errors detected exceeds a sensitivity threshold over a predetermined time period.

As a feature of this broad aspect, the step of determining the extent of the errors comprises a step of determining the number of errors detected.

As another feature of this broad aspect, the step of determining the extent of the errors comprises a step of determining the magnitude of the one or more values of the energy delivery parameter that exceed the predetermined threshold.

As another feature of this broad aspect, the step of determining the extent of the errors comprises a step of determining the duration of time during which the one or more errors are detected.

As another feature of this broad aspect, the energy delivery parameter is selected from the group consisting of: current, voltage, impedance and power.

As a feature of this broad aspect, the energy delivery device is an RF (radiofrequency) cutting device.

As an alternate feature of this broad aspect, the energy delivery device is an RF (radiofrequency) ablation device.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
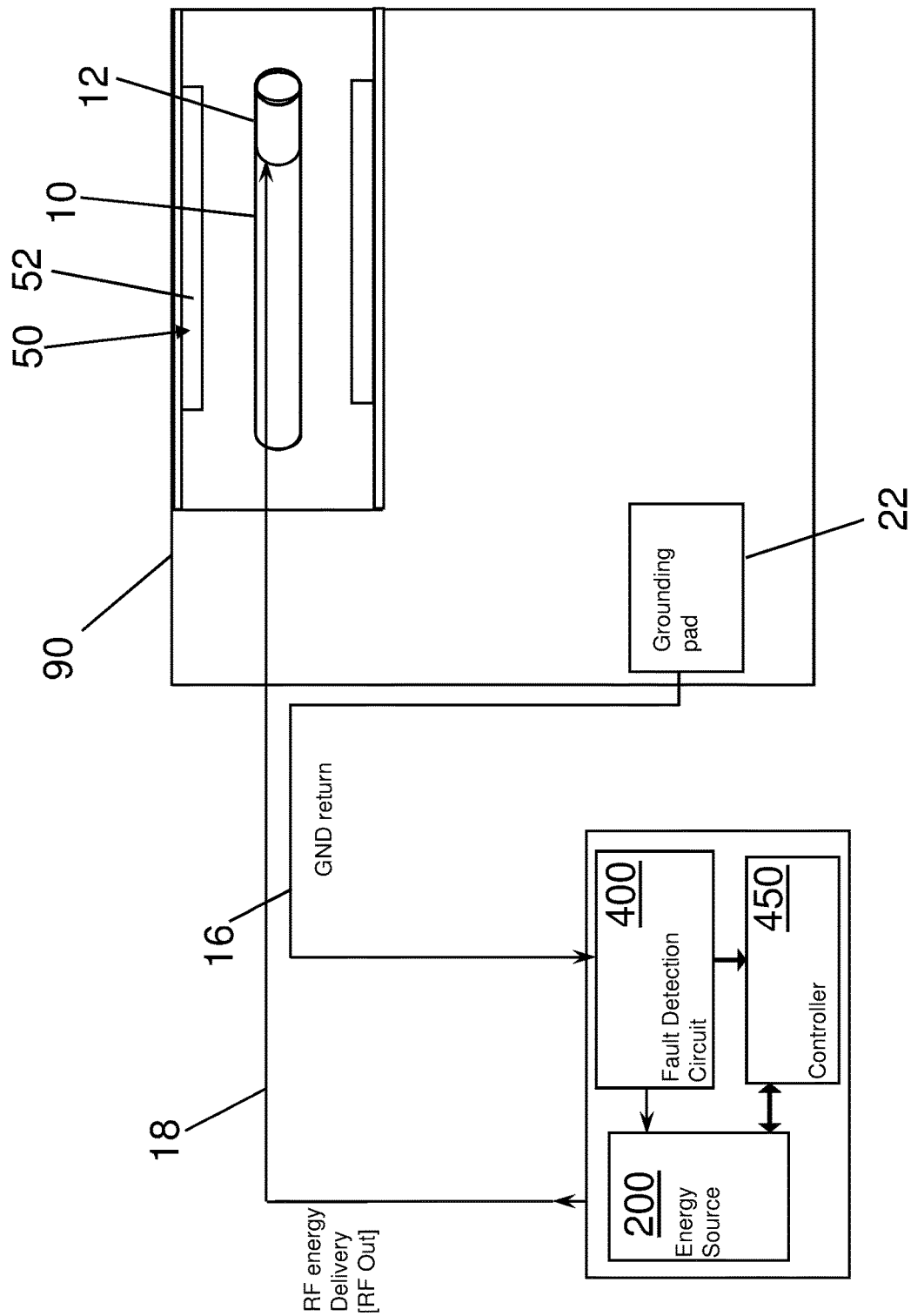
FIG. 1a is an illustration of a medical treatment system in accordance with an embodiment of the present invention.

In some medical applications, a radio-frequency medical device may be required in order to treat an area of tissue within a patient's body. The radiofrequency device may be used, for example, to either perforate through a region of tissue to create a pathway through a region of tissue or to ablate a region of tissue to create a lesion within the tissue. In some such medical applications, it may be necessary to use a radiofrequency medical device to treat a region of tissue that has an electrically conductive object positioned therein. For example, in some patients there may already be a stent present within the vasculature which has previously been placed to treat a medical condition, but which may have now become occluded or stenosed over time. Radiofrequency treatment may now be an option in order to create a passageway through the occlusion or stenosis within the stent lumen. However, the use of radiofrequency through or adjacent a conductive object such as a metallic stent creates a unique challenge. While it is desirable to use radiofrequency to traverse through a region of tissue such as an occlusion or stenosis, it is undesirable to apply radiofrequency while the medical device is too close to or in contact with the electrically conductive object as it may make the electrically conductive object an energy delivery conduit resulting in injury to the patient through excessive heating and/or charring of tissue around the electrically conductive object.

Conventional devices lack the ability to deliver energy near a conductive object while ensuring delivery is stopped or controlled if the device is too near or in contact with the electrically conductive object. Furthermore, convention devices lack the ability to provide the user with information about the proximity of the medical device to the electrically conductive object. As such there is a need in the art to provide an energy delivery system and method to allow a user to use radiofrequency energy to treat a region of tissue within the patient's body in the vicinity of an electrically conductive object while providing an indication of the proximity of the medical device to the electrically conductive object to allow the user to re-direct the medical device away from the conductive object.

Alternatively, in some medical procedures, it may be desirable to direct a medical device towards an electrically conductive object that may be positioned, for example, within a region of tissue within the patient's body to function as a target to direct the medical device to a desired target tissue location. The present inventors have recognized a need in the art for an energy delivery system that assists in navigation of a medical device towards a target site by providing proximity information between the medical device and the electrically conducive object.

The present inventors have thus discovered a method of delivering energy to a region of tissue within a patient's body using a medical device that is coupled to an energy delivery system. In accordance with an embodiment of the present invention, the method allows for use of a medical device near an electrically conductive object by providing proximity information that indicates the proximity of the medical device to the electrically conductive object. As such, in some embodiments the method and system of the present invention enable a user to direct a medical device away from an electrically conductive object while allowing the user to operate in the vicinity of the object by providing relative proximity information to the user that is relevant to the medical device and electrically conductive object. Some such embodiments provide for earlier detection as the device is approaching an object which may provide greater opportunity for course correction and may assist with successful completion of a medical procedure. In other embodiments, the method and system of the present invention allow the user to direct the medical device towards an electrically conductive target object and to guide the medical device towards a desired target location by providing an indication of the proximity of the medical device to the electrically conductive object. Particulars of such embodiments are described in Further detail herein below with respect to FIGS. 6a-6c.

Some embodiments of the present invention thus provide a method of delivering energy in a patient's body near an electrically conductive object in a safe and effective manner. In accordance with this approach, the present inventors have reduced to practice an embodiment of a method that detects if an energy delivery parameter of a medical device crosses a threshold and provides a relative measure of proximity between the medical device and the conductive object. In some embodiments, alternatively a method is provided that assesses the extent of the deviance or variance between the one or more measured values of the energy delivery parameter and the threshold to provide a relative measure of proximity between medical device and the conductive object.

Such embodiments are particularly useful and advantageous when a previous medical procedure has involved placement of a conductive object within the body and the treatment of the patient necessitates delivery of energy near or adjacent the conductive object while preventing contact with the conductive object. An example may be a region of vasculature that has an occlusion or stenosis at the site of a previous stent placement. Such embodiments are also particularly useful in procedures that require a medical device to be guided towards a desired target site where the target site may have a conductive object previously placed therein such as a guidewire or a snare. An embodiment of a method of the present invention is provided that assesses the proximity of medical device to the conductive object and provides information on the relative proximity between the two to guide the medical device towards the conductive object. This may help reduce procedural time and complexity for certain medical procedures such as for example a Transjugular Intrahepatic Portosystemic shunt (TIPS) procedure for example, as described in U.S. provisional application No. 62/208,404, filed on Aug. 21, 2015 and U.S. provisional application No. 62/208,138, filed on Aug. 21, 2015. These application are hereby incorporated by reference in their entirety. Detailed embodiments of such examples of the present invention are described in herein below with respect to FIGS. 6A-6C.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In accordance with an embodiment of the present invention, a method is disclosed for delivering energy within a region of tissue within a patient's body. The method helps avoid significant arcing while allowing use of an energy delivery device in the vicinity of an electrically conductive object such as a metallic object. An energy delivery parameter is monitored during the delivery of energy. The value of the energy delivery parameter is compared to a predetermined magnitude threshold to determine if the value exceeds or falls below the predetermined threshold to ascertain if there is significant arcing. The energy delivery is then controlled based on the extent of the arcing observed.

It should be understood that, throughout this specification, the terms "cross" or "exceed", in various forms, are used interchangeably to refer to the value of a parameter extending beyond the threshold, including both above the threshold (for example, in the case of an "upper threshold") as well as below the threshold (for example, in the case of a "lower threshold"). The terms "cross" or "exceed" may be used in either scenario and are not intended to be limited to either above or below the threshold.

Figure 1B:
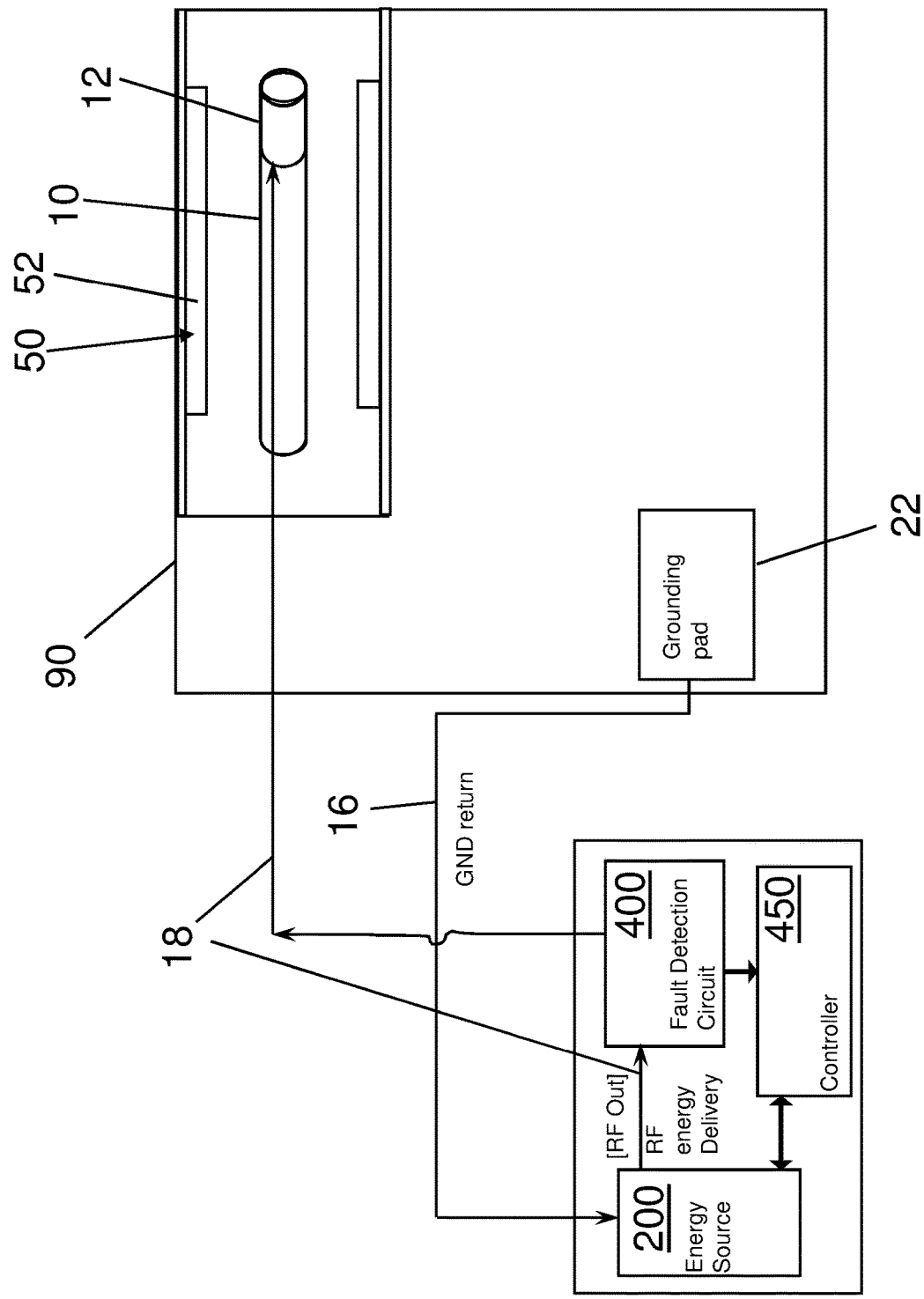
FIG. 1b is an illustration of a medical treatment system in accordance with an alternate embodiment of the present invention.

A medical treatment system, in accordance with embodiments of the present invention as shown in FIGS. 1a and 1b, comprises an energy delivery device or medical device 10 coupled to an energy source 200 to provide energy to a region of tissue within a patient's body. In one specific example, a radiofrequency (RF) energy delivery device is used in an electrosurgical application to cut or channel through a region of tissue. Energy is provided to generate an arc to enable cutting at the region of tissue. In some embodiments, as shown in FIGS. 1a and 1b, an energy delivery device 10 is used in a region of a patient's body 90 where an electrically conductive object 50, such as a metal object, is deployed or positioned. In such embodiments, the present invention allows for delivery of energy adjacent or near the electrically conductive object 50.

In one example, the electrically conductive object 50 is a stent 52 and an energy delivery portion 12 of an energy delivery device 10 may be positioned adjacent or close to the stent 52. Energy is provided by the energy delivery source or energy source 200 and through the energy delivery device 10 into the region of tissue. A change in an energy delivery parameter associated with the delivery of energy by the medical treatment system, may be observed due to the proximity of the stent 52 to the energy delivery portion 12. For example, a change in voltage, a lower impedance, an increased power output or an over-current or a current spike may be observed when there is arcing. The delivery of energy from the energy delivery device 10 may be prevented, for example by the system, if the arcing is significant and the extent of the arcing exceeds a sensitivity threshold. This may help avoid lesion formation by preventing RF energy from being transmitted through a low impedance metal object, such as stent 52. Thus, the delivery of energy from the energy delivery portion 12 of device 10 may be prevented when the energy delivery portion 12 of device 10 is positioned adjacent to or in contact with an electrically conductive object 50, for example, a metal object such as a stent.

In one embodiment of the present invention, a fault detection circuit 400, as shown in FIGS. 1a and 1b, may be used to monitor an energy delivery parameter such as current. If the energy delivery parameter crosses a predetermined threshold, the fault detection circuit 400 detects or records an error. In the embodiments described herein, an error may mean an error and/or a fault. In a specific example, if the monitored current is 2 Amps and it exceeds a current magnitude threshold of 1 Amp, an error in the form of an over-current is detected. The extent of the faults may be determined and the controller 450 may control the output of the energy delivery device based on the extent of the faults detected and/or recorded. If the extent of the errors exceeds a sensitivity threshold before the expiry of a predetermined time period, an event or alert may be triggered and energy delivery may be controlled. For the purposes of the present specification, "expiry of a predetermined time period" can mean, for example, (i) over a specific duration of time OR (ii) by a predetermined point in time relative to, for example, the beginning of the treatment procedure or the initiation of energy delivery. In one example, the 'extent' of the errors is measured over the course of a predetermined duration or time period.

As noted above, once the extent of the errors exceeds a sensitivity threshold, an event or alert may be triggered. In some embodiments, an energy delivery and control system may provide an indication to the user and may provide the user the option of disabling the energy. For example, the energy delivery and control system may provide an error warning or other alert to the user, for example on a screen associated with the energy source. Alternatively, the delivery of energy may be automatically affected based on the extent of errors detected. For example, energy delivery may be stopped or disabled, the delivery of energy may be reduced, and/or one or more of the energy delivery parameters may be altered.

In one embodiment, the extent of the errors may be ascertained by determining the resultant magnitude of the errors detected and/or recorded. In one embodiment, if the magnitude of the detected and/or recorded errors exceeds a predetermined sensitivity threshold, energy delivery may be controlled as described herein above.

In a specific example, as outlined above, if the monitored or measured current is 2 Amps whereby it exceeds a current magnitude threshold of 1 Amp, an error in the form of an over-current is detected. In further detail, the sensitivity threshold to measure the extent of the error(s) may be predetermined to be an amount of charge proportional to a 4 Amp current. For example, if five 2 Amp over-currents are detected, then the resultant total magnitude of these over-currents (i.e. the amount of the over-currents that is above the 'current magnitude threshold' of 1 Amp, added together), is determined. If this resultant magnitude of over-currents, which in this example would be equal to about 5 Amps (i.e. five over-currents where each exceeded the threshold by 1 Amp), exceeds the sensitivity threshold (4 Amps), an event may be triggered and energy delivery may be controlled.

In another example, if one 6 Amp over-current is detected (exceeding the threshold by 5 Amps), then the resultant magnitude of this single over-current (i.e. the amount of the current that is above the 'current magnitude threshold' of 1 Amp) is determined. If this resultant magnitude (which in this example is equal to 5 Amps) exceeds the sensitivity threshold (4 Amps), energy delivery may be controlled.

In one example, the energy delivery device comprises an RF wire. As shown in FIG. 1a, current in the RF return pathway or the ground (GND) return pathway 16 from a grounding pad 22 (monopolar operation) may be coupled to the fault detection circuit 400. In another example, ground (GND) return current from the energy delivery device (bipolar operation) may be coupled to the fault detection circuit 400. Alternatively, as shown in FIG. 1b, the RF output current at the output of the energy source (i.e. along the RF energy delivery pathway 18) is coupled to the fault detection circuit 400. In some embodiments, the fault detection circuit 400 may be a component of the energy source 200. In alternate embodiments, the fault detection circuit 400 may be coupled to the energy source 200 through a controller 450. In other embodiments, the fault detection circuit may be a separate entity and may be operable to be used with any RF generator. A relay may be used to turn off or disable RF energy delivery in response to the detected fault(s).

The energy delivery parameter may be monitored continuously or intermittently. Also, the energy delivery parameter may be monitored either during the delivery of energy (i.e. concurrently with the step of delivering energy) or shortly after the step of delivering energy (i.e. energy delivery and monitoring may be performed in an alternating manner). In other words, the steps of delivering energy and monitoring may be performed either contiguously or substantially simultaneously. Furthermore, in some embodiments, the energy may be delivered continuously, intermittently or in a pulsed manner.

The monitored energy delivery parameter may be any one of, or a combination of, current, voltage, impedance or power. Alternatively, other suitable energy delivery parameters may be used and monitored. For example, if a decrease in output impedance or voltage, or an increase in output power or current, is detected by a fault detection circuit, one or more errors may be detected and/or recorded. Thus, if a value of the energy delivery parameter is not within a predetermined range or crosses or exceeds or does not meet a specified magnitude threshold, one or more errors may be detected and/or recorded. In other words, if the value of the energy delivery parameter falls below a predetermined magnitude threshold or exceeds a specified magnitude threshold (i.e. if the energy delivery parameter crosses a magnitude threshold) an error is detected.

Additionally, an extent, for example the quantity or quality, of any such detected errors may be determined or assessed. The delivery of energy may be controlled in response to the extent of errors detected. For example, the delivery of energy may be controlled if the quantity or quality of the detected exceeds a sensitivity threshold before the expiry of a predetermined time period. In some embodiments, the sensitivity threshold may be defined by a threshold number of errors, a threshold value of the energy delivery parameter or a time threshold. In alternate embodiments, the sensitivity threshold may be defined in terms of a threshold limit of an amount of charge that can be accumulated before energy delivery is controlled. In some embodiments, the sensitivity threshold may be a voltage threshold. In one particular embodiment, the sensitivity threshold may be a voltage threshold associated with the amount of charge that can be stored by a capacitor.

In some embodiments, the step of determining the extent of errors detected may comprise a step of determining the number of errors detected. In such embodiments, energy delivery may be controlled if the number of faults or errors exceeds a threshold quantity (i.e. if the amount of errors detected, regardless of the absolute value of each error, exceeds a predetermined threshold) before the expiry of a predetermined time period.

In other embodiments, the step of determining the extent of errors detected may comprise a step of determining the resultant magnitude of the one or more detected values of the energy delivery parameter. The delivery of energy from the energy delivery device may be controlled in response to the resultant magnitude of the one or more values of the energy delivery parameter. More specifically, energy delivery may be controlled if the resultant magnitude (or in other words sum) of the one or more values of the energy delivery parameter exceeds a threshold value before the expiry of a predetermined period of time. For example, the energy delivery parameter may be current, and charge from any over-currents may be stored in a capacitor. If sufficient charge is accumulated before the capacitor discharges completely, an event may be triggered and energy delivery may be controlled. In one example, the sensitivity threshold may correspond to a current value of 4 Amps which may correspond to the amount of charge that can be stored by the capacitor. If two 3 Amp over-currents (that each exceed a magnitude threshold of 1 Amp) are detected, then the capacitor may become fully charged (depending on the rate of discharge of the capacitor, fully charging the capacitor may require slightly more over-current to be detected) and the energy delivery may be controlled in response.

In still another embodiment, the step of determining the extent of errors detected may comprise a step of determining the duration of time during which the one or more errors are detected. In other words the extent of the error is determined by measuring the length of time, or duration, over which the error existed. The delivery of energy from the energy delivery device may be controlled in response to the duration of time during which the one or more faults are detected. Energy delivery may be controlled if the duration of time for the one or more faults detected exceeds a time threshold before the expiry of a predetermined period of time. In some embodiments the time threshold may be less than the predetermined period of time. In other embodiments, the time threshold may be equal to the predetermined period of time.

In some embodiments, the monitored energy delivery parameter may be current and the extent of the over-currents detected within a time period may be determined. The controller 450 may adjust the delivery of energy through the energy delivery source 200 based on the extent of the over-currents detected/recorded. As described above, in one example, the power may be shut off or the energy delivery otherwise disabled if the number of over-currents detected exceeds the sensitivity threshold before the expiry of a time period. If a large number of over-currents are detected, an event may be triggered and energy delivery may be disabled. As an illustration of this embodiment, the sensitivity threshold for the quantity of over-currents detected may be preset to about 10. If the number of over-currents detected exceeds 10 within, for example, a time period of about 300 us, an event is triggered and energy delivery may be controlled.

In some embodiments, the monitored energy delivery parameter may be impedance. One or more errors may be detected, if, for example, the impedance seen by the device falls below a threshold impedance limit. In one example, the initial value of the measured impedance may be in the range of about 200Ω. As energy is delivered via the energy delivery device, the measured impedance may rise to be in the range of about 1500Ω. Once arcing is initiated the measured impedance may drop to below about 100Ω. In one example, as the impedance drops below the threshold impedance, which may be, for example, 100Ω, one or more errors may be detected. After an arc is observed, the measured impedance may rise again to about 1500Ω. Once another arc is observed, the measured impedance may drop once again to below about 100Ω. In one example, the extent of the errors may be determined by determining the number of times the measured impedance drops below about 100Ω. Energy delivery may be controlled if the extent of errors detected is greater than the sensitivity threshold. In the aforementioned example, the sensitivity threshold may be defined as a predetermined number of errors. Energy delivery may be controlled if the number of times the impedance drops below the threshold impedance (e.g. 100Ω), before the expiry of a time period, is greater than the predetermined sensitivity threshold number. Thus, the delivery of energy from the energy delivery device may be controlled in response to the number of errors detected before the expiry of a predetermined time period.

In another example, the measured impedance may remain at or below about 100Ω for some time. In such an example, the extent of the errors may be determined by determining the duration of time over which the impedance drops below the threshold impedance. The energy delivery may be controlled if the extent of errors detected exceeds a sensitivity threshold which, in this example, may be defined as a time threshold. Thus, energy delivery may be controlled, if the duration of time during which impedance is below the threshold impedance exceeds the time threshold (before the expiry of a predetermined time period). In some embodiments, the time threshold may be equal to the predetermined time period. In other embodiments, the time threshold may be less than the predetermined time period.

In one example, the monitored energy delivery parameter may be current from the Ground Return (GND) of the energy delivery device or the output current from the energy source in the energy delivery pathway. The current may be monitored using a fault detection circuit 400 as shown in FIGS. 1*a*, 1*b* and FIGS. 2 and 3. Whenever a current spike is detected, it may constitute an error and the error can be detected and/or recorded. In other words, when the measured current crosses or exceeds a predetermined current threshold (for example, either during the positive or negative cycles of an RF waveform), an error in terms of an over-current is detected. The extent of the errors or faults in terms of over-currents may then be determined or assessed. If the extent of these over-currents exceeds a sensitivity threshold before the expiry of a predetermined time period, energy delivery may be controlled by the controller 450. In one embodiment, the extent of the over-currents may be ascertained by determining the resultant magnitude of the over-currents detected. In one embodiment, if the magnitude of the detected and/or recorded over-currents exceeds a predetermined sensitivity threshold, energy delivery may be controlled. In one example, a capacitor, such as capacitor 516*a* shown in FIG. 4*a*, may be used to determine the resultant magnitude of the detected over-currents. In other words, the amount of charge from the over-currents (that exceeds the magnitude threshold) is accumulated and stored within the capacitor. The charge may be periodically discharged by the capacitor. Thus, as charge accumulates on the capacitor some of it is discharged intermittently by the capacitor in between over-currents. Once enough charge has accumulated on the capacitor an event may be triggered and energy delivery may be controlled as described hereinabove.

In one example, the extent of the over-currents detected may involve determining the number of over-currents detected. The sensitivity threshold may be determined by a set number or quantity of over-currents that have to be detected and/or recorded before energy delivery is controlled. If the number of over-currents detected exceeds a predetermined quantity, an event can be triggered which disables energy delivery. Thus, the sensitivity threshold may be defined or adjusted such that energy delivery is not disabled until after a predetermined number of over-currents or arcs have been detected and/or recorded. This allows the physician to continue to cut and steer away after an over-current or arc is detected. The output energy stays at the nominal value required for RF cutting and as the energy delivery device or medical device 10 is moved away from the metal object it can continue to cut. Thus, the orientation or position of the energy delivery portion 12 may be re-adjusted by moving it around or away from the electrically conductive object 50 such as a metal object, even if a few over-currents are detected while power is being delivered. This allows a user to cut close to the metal object. This further allows steerabilitiy of the device around the low impedance metal object and allows a pathway to be created by cutting around or close to the metal object. In one specific example, the user may continue to cut and create a pathway in a vessel lumen, such as through an occlusion or a stenosis at the location where a stent has been deployed. The energy delivery device or medical device 10 may continue to deliver energy and cut while traversing through a stent lumen positioned within a body lumen, such as a blood vessel. Thus, depending on the setting of the sensitivity threshold, even after several over-currents, the user can steer device 10 away from the stent while continuing to deliver energy.

Figure 4A:
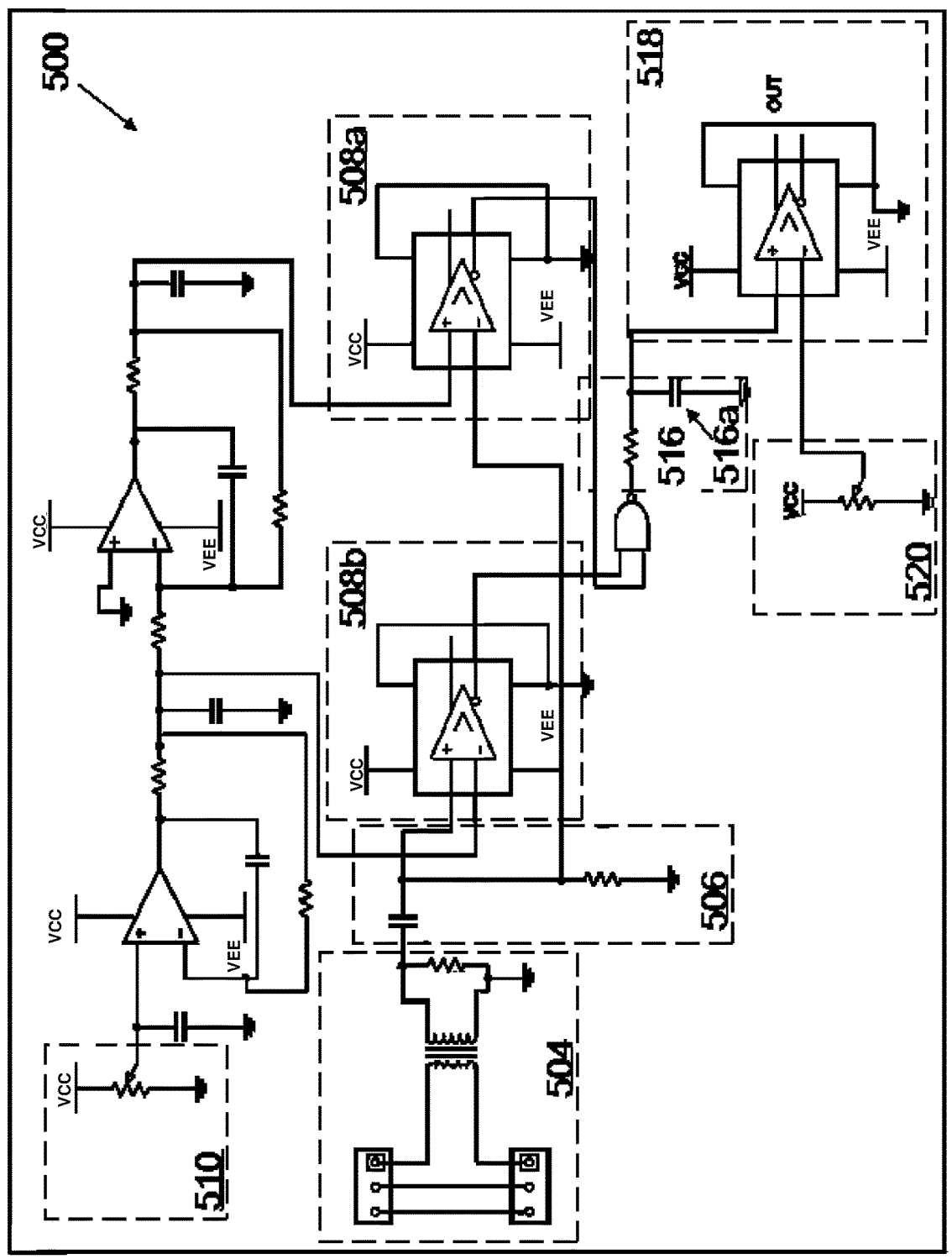
FIG. 4a illustrates a circuit diagram of a fault detection circuit in accordance with an embodiment of the present invention.
Figure 4B:
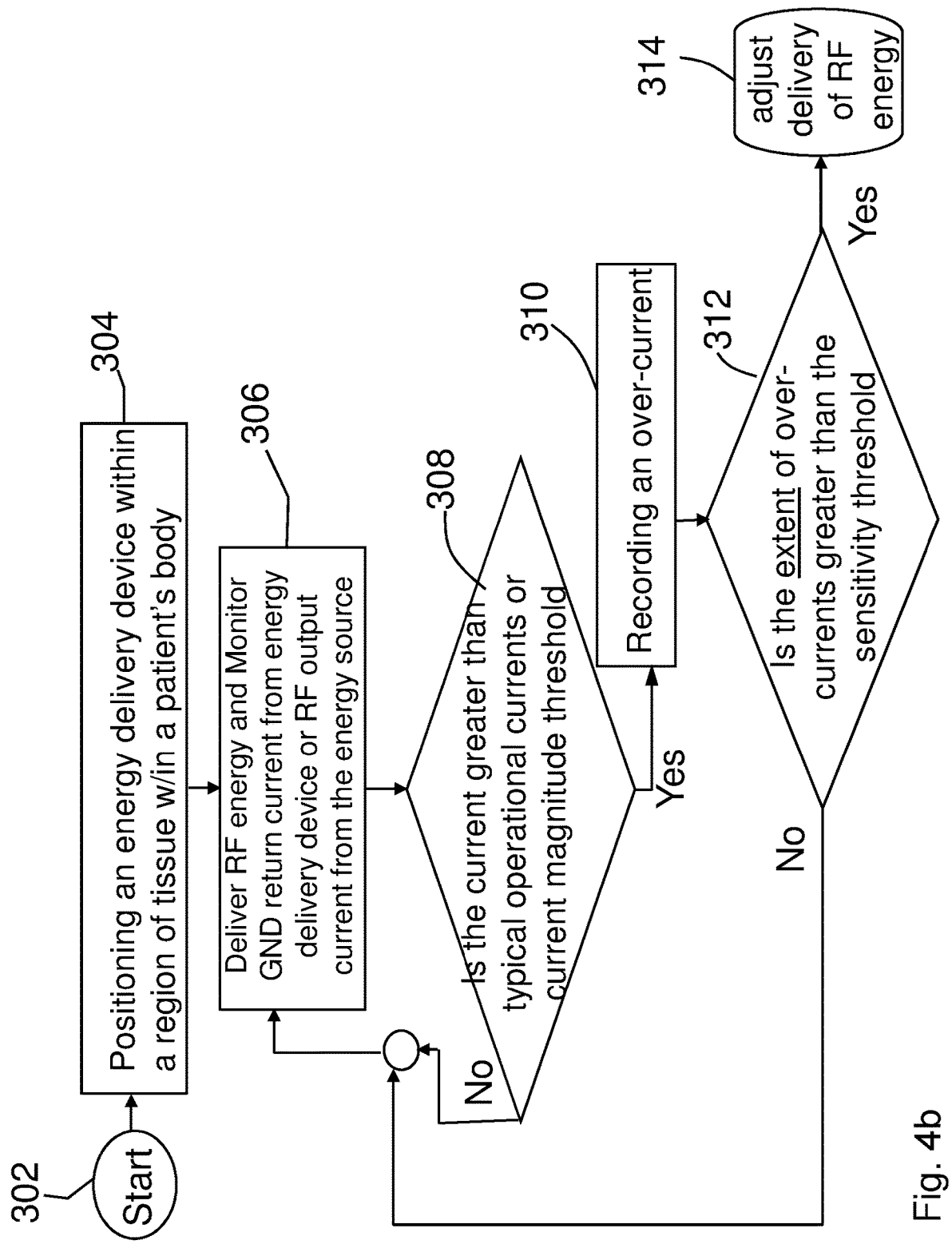
FIG. 4b is a flow chart showing a method in accordance with an embodiment of the present invention.

In accordance with one broad embodiment of the present invention, a method is disclosed for delivering energy to a region of tissue within a patient's body. FIG. 4b is a flow chart illustrating an example of such a method. As shown by step 304, an energy delivery device may be positioned within a region of tissue at a target location within a patient's body. At step 306, an RF power source may be used to supply RF energy to the energy delivery device. The energy delivery parameter that is monitored may be the current output from the ground return pathway of the energy delivery device. The measured values of the current are compared to a predetermined current range or magnitude threshold. In one example, the range of currents or current threshold may reflect normal operational currents required for cutting. In another example, the current magnitude threshold may reflect normal operational currents generated during RF ablation. The current magnitude threshold may be an adjustable threshold. In one specific example, the energy delivery device is an RF cutting device and the normal operational threshold currents are in the range of less than about 3 Amperes (Amps). In another example, the threshold current may be less than about 2 Amps. In another example, the threshold current may be less than about 1 Amp. In still another example, the threshold current may be in the range of between about 2 Amps to about 3 Amps. In another embodiment, the energy delivery device may be a radiofrequency ablation device and the normal operational current threshold may be less than about 1 Amp. In another example, the threshold current may be about 1.5 Amps.

At step 308, the measured current is analyzed to determine if it is greater than the predetermined threshold or range. If the current has peak values that exceed the current magnitude threshold or normal operational currents, at step 310 an excess current or over-current is recorded. If the monitored current is within the range of normal operational currents (below the predetermined current threshold), then the delivery of energy through the energy delivery device will not be interrupted and energy delivery can continue at step 306 and the current can continue to be monitored. At step 312, a determination is made to assess whether or not the extent of over-currents recorded within a time period is greater than the sensitivity threshold and, if it is, then the energy delivery may be adjusted at step 314. In one example, energy delivery may be stopped. In some embodiments, the extent of over-currents recorded may be determined in terms of the sum or magnitude of the over-currents recorded. In other embodiments, the extent of over-currents recorded may be determined in terms of the number or quantity of over-currents recorded. If the extent of over-currents is still below the sensitivity threshold, then at step 306 the energy delivery is continued while monitoring the current.

Referring back to FIGS. 2 and 3, a fault detection circuit 400 may be used to determine if the energy delivery portion 102 of device 100 is near or adjacent to an energy conductor such as a stent 52 or a snare during RF delivery. The fault detection circuit 400 may be used to detect, for example, currents in the ground (GND) return path of the energy delivery device 100 or currents at the RF output 18 of the energy source in the energy delivery path. If peak currents or over-currents are detected that exceed typical predetermined operational currents, an event may be triggered and energy delivery through device 100 may be stopped or otherwise affected. The fault detection circuit 400 may be integral with the RF energy delivery source 200, which may be an RF generator. In other embodiments, fault detection circuit 400 may be a separate component of the medical treatment system. In one example, the fault detection circuit 400 may receive input current from the ground return pathway 16 from a grounding pad positioned on the patient's body in a monopolar application. Alternatively, the fault detection circuit 400 may receive input current from a ground return pathway from the energy delivery device 100 in a bipolar application (not shown).

Figure 2:
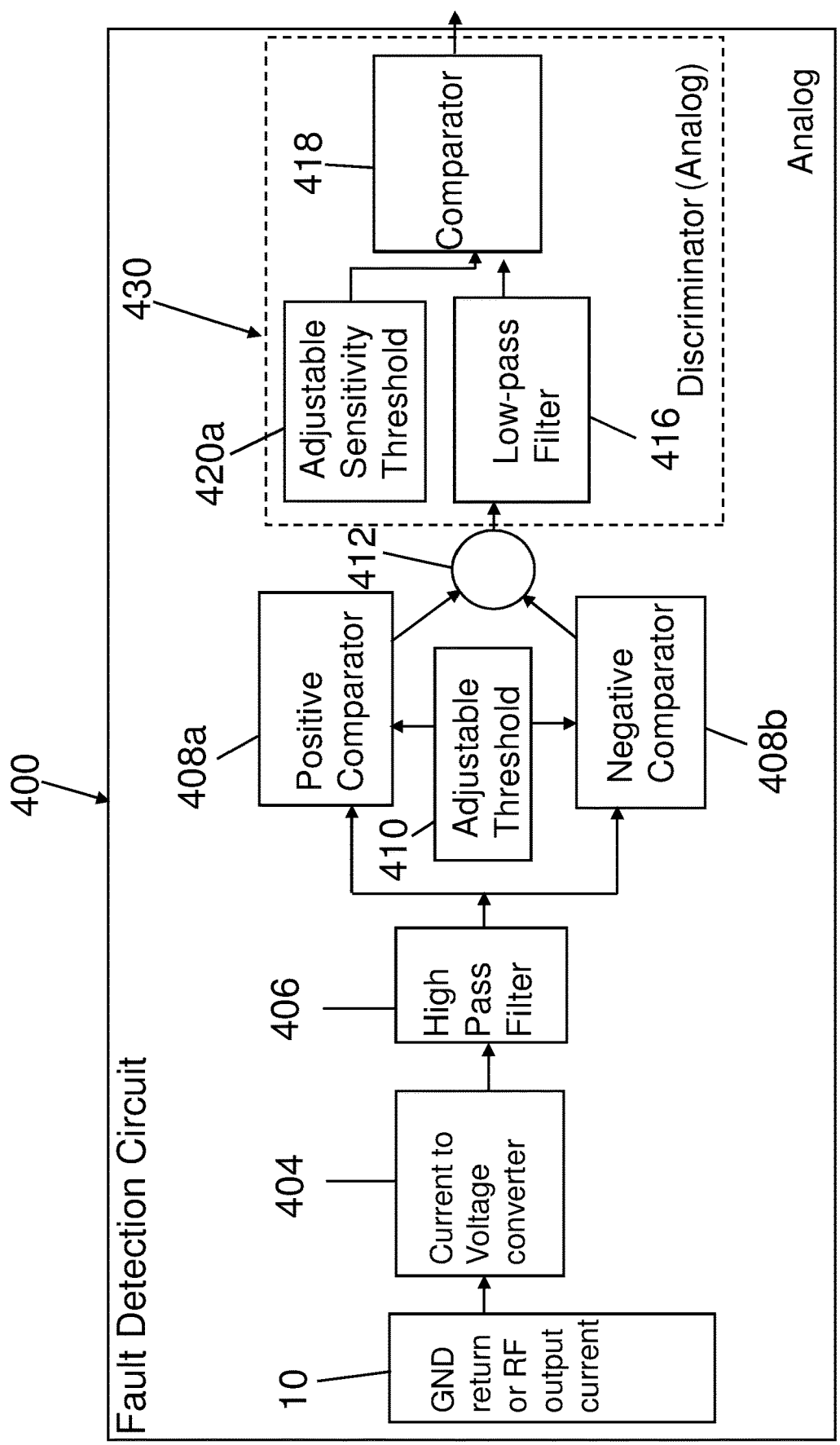
FIG. 2 illustrates a block diagram of a fault detection circuit in accordance with an embodiment of the present invention.
Figure 3:
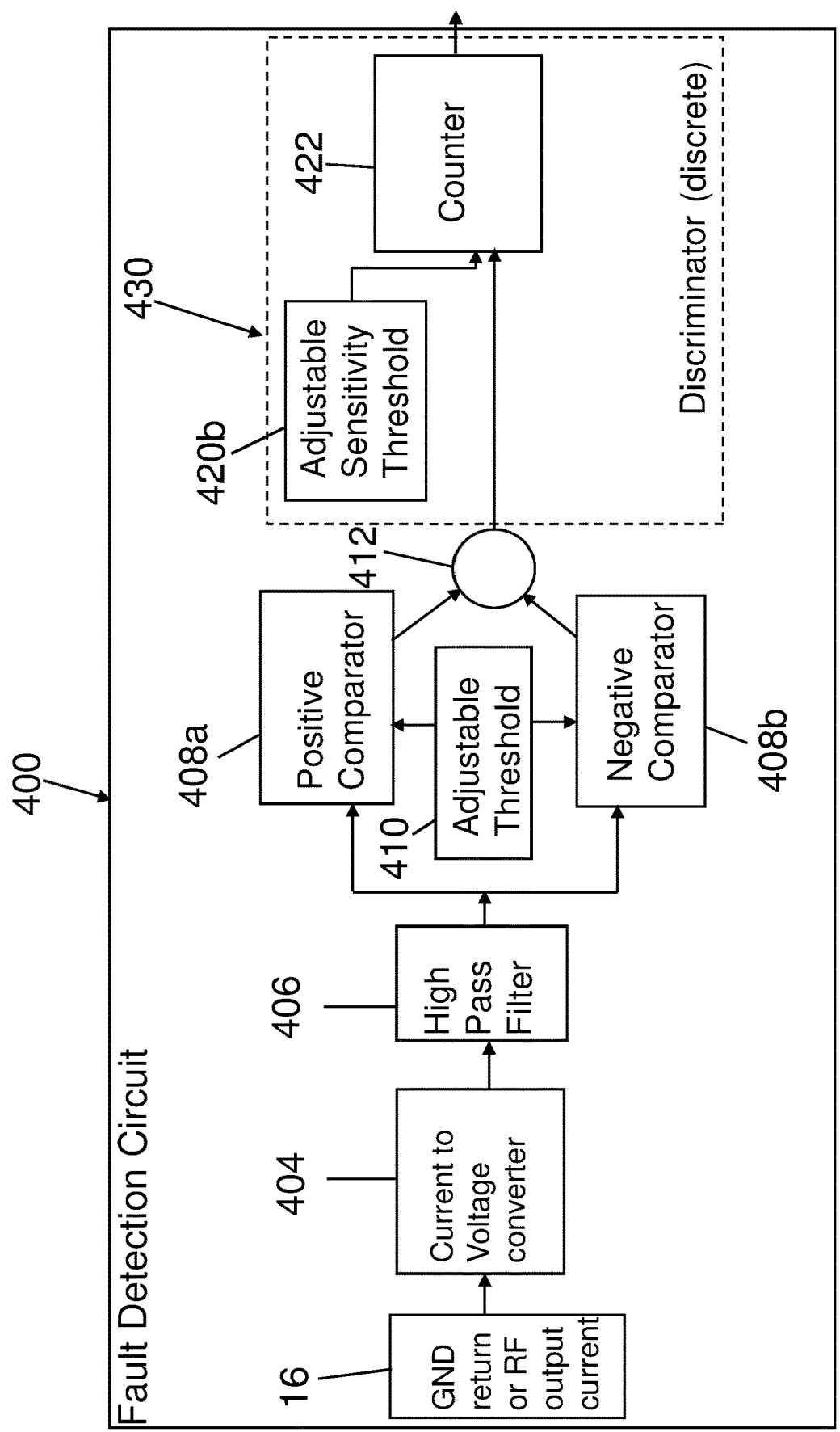
FIG. 3 illustrates a block diagram of a fault detection circuit in accordance with an alternate embodiment of the present invention.

The input current may be sensed using a current to voltage converter 404 as shown in FIGS. 2 and 3, which converts the measured current (either at RF output or GND return) of the device into voltage. In some embodiments, a voltage sense transformer may be used. In other embodiments, any current to voltage converter, for example a current sense transformer, may be used. In still other embodiments any means to sense the current may be used. In one specific example, a current sense transformer 504 is used as shown in FIG. 4a, and the output of the current sense transformer 504 may be connected to a high-pass filter 506. The high-pass filter allows for adequate rejection of the fundamental or operating frequency of the RF system. This may aid in detection of over-currents. The high-pass cut off can change based on the operational frequency. In one specific example, as shown in FIG. 4a, the high pass filter is an RC filter 506. The RC filter can be a single pole filter or a multi-pole filter. The output of filter 506 may then be routed to an input comparator 408a, which, in this example, is a positive comparator that can detect positive current peaks. An additional input comparator may be used such as a negative comparator 408b that has the ability to detect negative current peaks. In one example, comparators 508a, 508b may be used as shown in FIG. 4a.

The circuit may have an adjustable voltage threshold 410 which may be achieved through the use of a potentiometer 510 as shown in FIG. 4a. In other words the input comparators 408a, 408b may have an adjustable voltage threshold. This allows the current threshold for detecting over-currents to be adjusted as desired. In alternate embodiments the voltage threshold may be fixed. The output of the input comparators 408a, 408b may be fed into the Discriminator circuit 430. In one example, as shown in FIG. 2, the Discriminator Circuit 430 has an analog implementation which allows the magnitude of the over-current(s) to be recorded. In other words, the extent of the over-currents detected is determined in terms of the sum of the magnitude of the over-currents detected. I.e. the actual values of the currents that are above the magnitude threshold have been recorded and are added together.

As the high-frequency current peaks (over-currents) are detected by the two input comparators 408a, 408b, the over-currents are fed into, for example an OR gate 412 to create a pulse train. In the embodiment shown in FIG. 2, as noted above, the Discriminator Circuit 430 has an analog implementation. The Discriminator circuit 430 has a low pass filter 416 which presents a slowly-changing average of this pulse train to the output comparator 418 of the Discriminator circuit 430. If the pulses are frequent enough, the voltage at the input of comparator 418 will rise above the sensitivity threshold and will trip the Discriminator Circuit output.

The low pass filter 416 may help reduce the risk of false positives in terms of false over-currents being detected. In one example, the low pass filter 416 may be an RC filter 516 at the input of the comparator. The RC filter 516 allows the charge from the detected over-currents to be stored within capacitor 516a. The charge from an over-current or cumulative charge from multiple over currents is stored by the capacitor 516a within the RC time constant of the capacitor. In one example, the RC time constant of the capacitor is about 100 μs. The voltage at the capacitor 516a node is fed as an input of the output comparator 518. When the voltage at the capacitor 516a node is equal to or greater than the sensitivity threshold voltage input to the output comparator 518, this determines that the extent (i.e. in this embodiment, the sum, or in other words, the resultant magnitude) of the detected over-currents exceeds the sensitivity threshold.

In one example, the sensitivity threshold may be fixed. In another example, the output comparator 418 may have an adjustable sensitivity threshold 420a. In one example a potentiometer 520 may be used to adjust the sensitivity threshold by changing the voltage at the input of the output comparator 418. This changes the voltage to which the capacitor 516a must charge and proportionately the length of time required for the charge to accumulate on the capacitor 516a. If the potentiometer is set to a higher voltage, than a greater number of over-currents may occur before the controller allows the power supply to the energy delivery device to be shut off, thereby disabling energy delivery. In one example, the sensitivity threshold may be set to allow 10×1 Amp current peaks or over-currents to be detected within a 100 μs time period prior to disabling the energy delivery. Alternatively, or in addition, the sensitivity threshold may allow 5×2 Amp current peaks or over-currents to be detected. In another embodiment, the sensitivity threshold may be set to allow, for example, 10×3 Amp current peaks to be detected within a 100 μs time frame. Other examples are possible as well.

The output of the comparator may then be conveyed to a controller, which controls the delivery of energy through the energy delivery device. In one embodiment, the controller may prevent the delivery of energy through the energy delivery device based on the sum or magnitude of over-currents detected. In other words the controller may shut-off the power delivery based on the extent of over-currents detected.

With reference now to FIG. 3, an alternate embodiment is shown in which the Discriminator Circuit 430 comprises a discrete or digital implementation. The number of current peaks may be detected and, rather than a low-pass filter and comparator, a digital counter 422 may be used. The digital counter 422 may have an external reset. In one example, if the number of over-currents detected before the counter is reset exceeds a digital threshold, the energy delivery may be disabled. The sensitivity threshold in the digital implementation of the Discriminator circuit 430 is the digital threshold, which represents the number of pulses or over-currents that should be detected before the output of the Discriminator Circuitry 430 is asserted and conveyed to the controller. The controller may then control the delivery of energy through the energy delivery source based on the number of over-currents detected. In one example, the digital sensitivity threshold 418b may be variable, or may be adjustable by the user. In this example, the number of over-currents that must be detected by the counter 422 before an output is asserted, can be changed as desired by the user. In another embodiment, the sensitivity threshold may be fixed and the number of over-currents that must be detected by the counter 422 may thus be fixed as well.

Figure 5A:
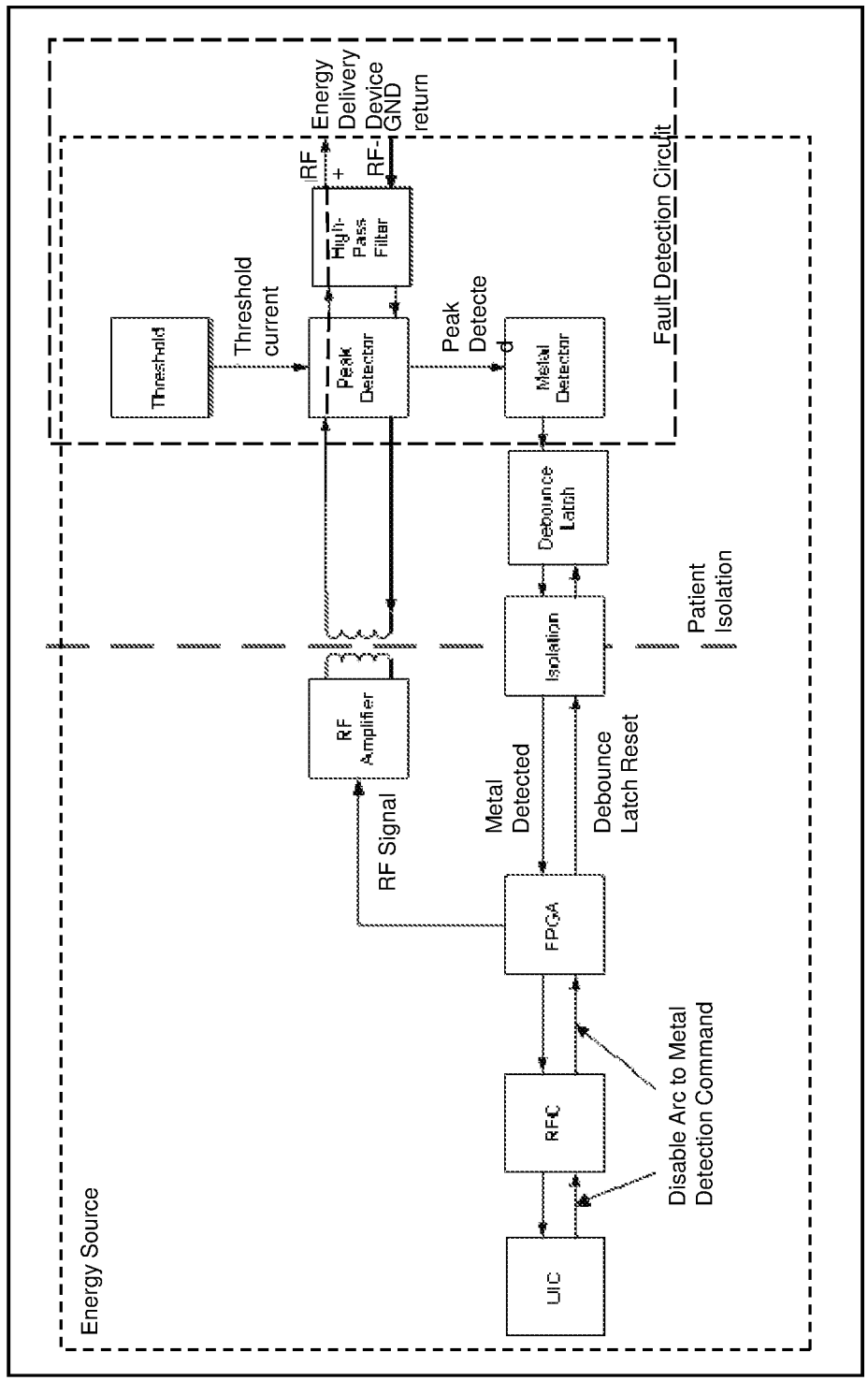
FIG. 5a illustrates a block diagram of an energy delivery system in accordance with an embodiment of the present invention.
Figure 5B:
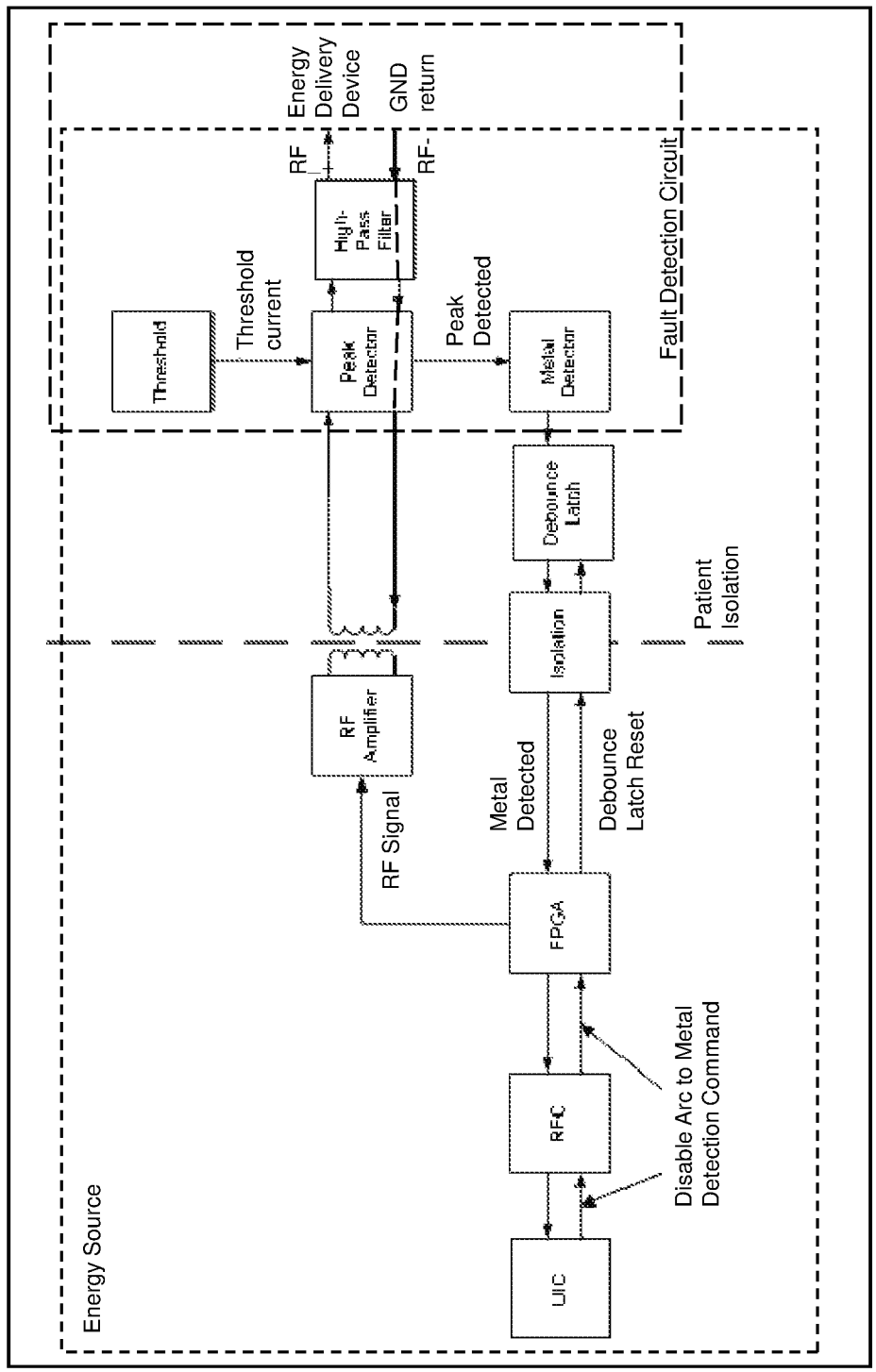
FIG. 5b illustrates a block diagram of an energy delivery system in accordance with an alternate embodiment of the present invention.

With reference now to FIGS. 5a and 5b, block diagrams of a medical treatment system in accordance with embodiments of the present invention are shown. An energy delivery source is shown which includes a fault detection circuit. In some embodiments the fault detection circuit may be a separate component of the medical treatment system. In one example, the fault detection circuit receives input from the ground return as indicated by "RF−", in FIG. 5a. In another example, the fault detection circuit receives input from the RF Amplifier of the energy delivery source, as shown in FIG. 5b.

The RF Amplifier of the energy delivery source of the generator provides input current to the energy delivery device shown as "RF+". The RF amplifier is coupled to an FPGA (field programmable gate array) which may be coupled to an RF board Controller (RFC) and a User Interface Controller (UIC) which help control the output to the energy delivery device. The Control circuitry, which includes the RFC, the UIC and the FPGA, receives feedback from the fault detection circuit and can control the delivery of energy from the energy delivery source based on the input received from the fault detection circuit. Once the Discriminator Circuit (not shown) of the fault detection circuit determines that the extent of the over-currents (magnitude or sum of over-currents) exceeds a sensitivity threshold, the output generated by the Fault Detection Circuit may be conveyed to a latch and its output may be set to high. This output may then be conveyed to the Control Circuit, which allows the energy delivery from the energy delivery source to be controlled based on the output of the Fault Detection Circuit. Thus the delivery of RF signal from the RF amplifier may be stopped. The latch output may then be reset. In some examples, the latched signal is detected via serial read or interrupt. (The Peak Detector and High Pass Filter of the Fault Detection Circuit do not impede flow of RF current, but rather monitor it). The medical treatment system may also include a feature allowing a user to disable the arc-to-metal-detection function.

With further reference to FIGS. 5a and 5b, the current from the output of the energy delivery device is received as input into the current to voltage converter and high pass filter. In a specific example, the high pass filter is a 1.5 MHz nominal −3 db point single-pole high pass filter. Furthermore, in one specific example, the Peak Detector activates for current spikes of either polarity that exceed 40 ns in duration at a threshold current value of 1.7 A. In other words the Peak Detector detects an error/fault if the current exceeds 1.7 A for a duration of at least about 40 ns. The energy delivery is then controlled if the extent of errors or faults detected exceeds a sensitivity threshold. The sensitivity threshold may be defined or set based on one or more of the magnitude (in terms of the amplitude) as well as the pulse width of the pulse train of current to be detected. In one embodiment, the sensitivity threshold is set as a time threshold or duration of about 300 μs±30 μs. In an example of this, if pulses (that are at or above a threshold amplitude of 1.7 Amps having a pulse width of about 113 ns) are observed for a duration of at least about 300 μs±30 μs, energy delivery may be controlled. More specifically, once the Peak detector has been supplied with a continuous string of pulses for duration equal to or exceeding the sensitivity threshold of about 300 μs±30 μs, the Metal Detector within the Fault detection circuitry is activated.

In another example, the sensitivity threshold is set as a time threshold or duration of about 30 μs±3 μs. If pulses (that are at or above the threshold amplitude of 1.7 Amps having a pulse width of about 500 ns) are observed for a period of time greater than or equal to about 30 μs±3 μs, the energy delivery may be controlled. Thus, once the Peak detector has been supplied with a continuous string of pulses (having a pulse width of at least about 500 ns) for duration equal to or exceeding a sensitivity threshold of about 300 μs±3 μs, the Metal Detector is activated. The output generated by the Fault Detection Circuit may then be conveyed to the Control circuitry to modify the output of the energy delivery device.

As mentioned above, the Control circuitry which includes the RFC, the UIC and the FPGA receives feedback from the fault detection circuit and can control the delivery of energy from the energy delivery source based on the input received from the fault detection circuit.

In alternate embodiments, the energy delivery device may be used near an electrically conductive object 50 that is a bare metal snare. In still another example, the electrically conductive object 50 may be an RF wire. In further examples, the electrically conductive object 50 may be any metal object positioned within a patient's body such as a metal screw. In one example, the electrically conductive object 50 may be a metal RF wire or a snare that may be used as a target for positioning the energy delivery device. In some embodiments, the electrically conductive object 50 may be another electrosurgical device. In one specific example, the electrically conductive object or device 50 may be a stent-graft and the medical treatment system may be used to create a fenestration through a stent-graft through the delivery of RF energy. In other words, the RF energy delivery device may be used to induce graft perforation of a stent-graft as discussed in U.S. patent application Ser. No. 11/905,448, filed on Oct. 1, 2007, previously incorporated herein by reference in its entirety. In one example, the stent-graft may be positioned in a renal artery. In another example, the stent-graft may be positioned in a branch of the aorta. In one specific example, the medical treatment system may be used to create a fenestration through a stent-graft positioned in the thoracic aorta.

In various alternatives, the energy delivery device 10 may have an electrically conductive energy delivery portion 12 along at least along a portion of the energy delivery device. The energy delivery portion 12 is coupled to the energy source 200 such that the energy delivery source 200 provides RF energy to the energy delivery portion 12. The energy delivery portion 12 may comprise one or more active electrodes positioned on a portion of the energy delivery device 10. In one embodiment, the energy delivery device is an RF energy delivery device that comprises at least one active electrode. In other embodiments, more than one active electrode may be positioned on the energy delivery device.

In some embodiments of the present invention as disclosed above, the energy source may provide energy in the range of between about 100 KHz to about 1.5 MHz. In one example the energy source is provided in the form of an RF generator that is capable of delivering energy in the frequency range of between about 400 KHz to about 550 KHz, more specifically, between about 450 KHz to about 480 KHz. In one example, energy is delivered at a frequency of about 460 KHz. The energy delivery device may be used to provide energy for a range of applications within a patient's body. This may include use in cardiac applications, for treatment within a patient's vasculature.

In some embodiments, power may be provided at greater than about 30 Watts. In some embodiments, the power may be supplied at greater than about 50 Watts. The voltage supplied may be greater than 200 Vrms. In some embodiments the energy delivery device may be an RF cutting device. In some such embodiments, the voltage is supplied in the range of between about 200 Vrms to about 300 Vrms. In some embodiments, the voltage may be supplied in the range of between about 200 Vrms and 400 Vrms. In other embodiments, the supplied voltage is greater than or equal to about 400 Vrms.

In an alternate embodiment, the energy delivery device may be an RF ablation device with an active ablation electrode. In some embodiments, the voltage supplied may be greater than about 50 Vrms. The power may be supplied in the range of between about 2 Watts and about 8 Watts. In some such embodiments, the Voltage may be between about 100 Vrms to about 200 Vrms.

Figure 6A:
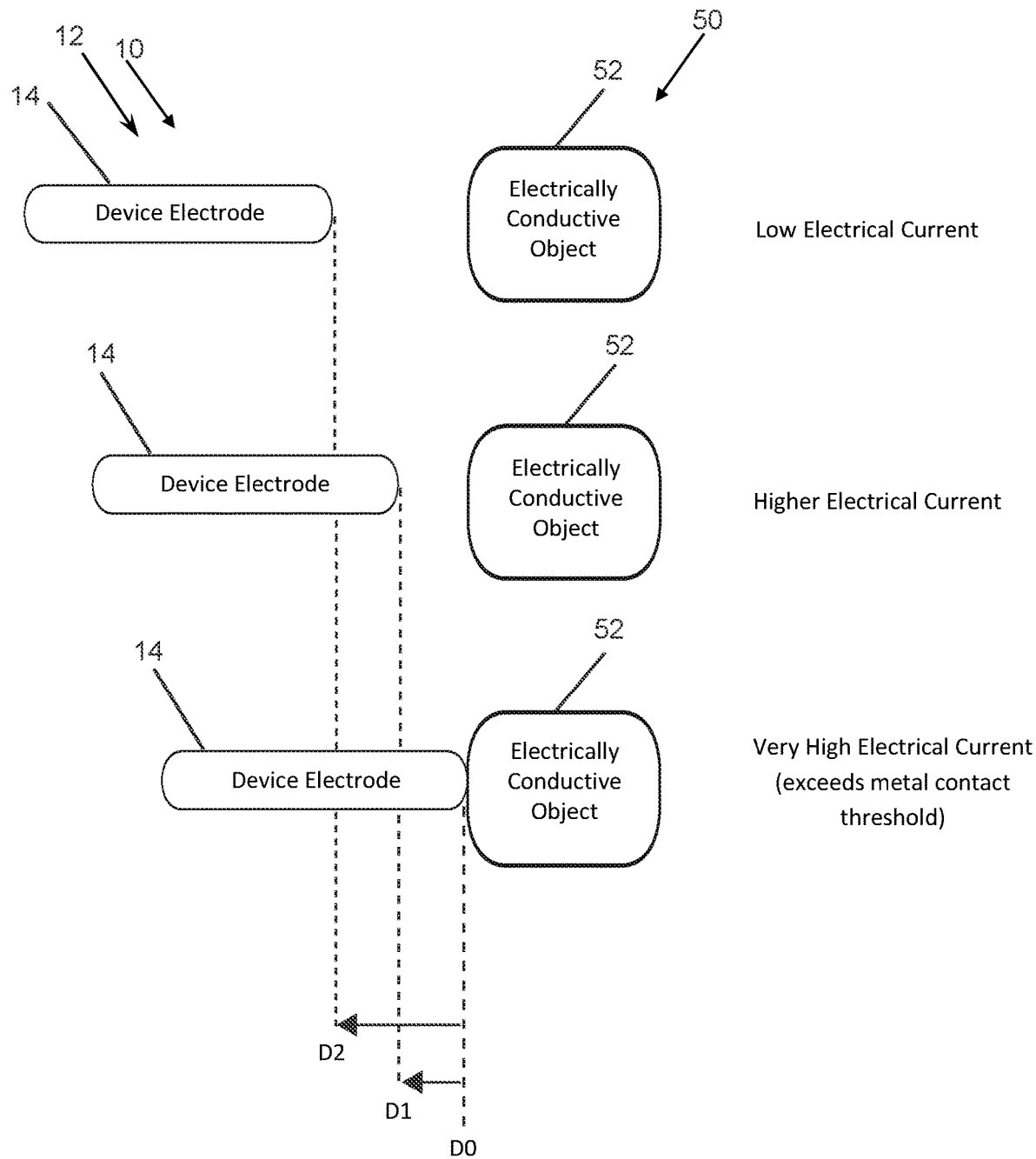
FIG. 6a illustration of a method and system in accordance with an embodiment of the present invention.

In one particular embodiment, as described previously and as described further with reference to FIG. 6a, a method is disclosed for delivering energy within a region of tissue within a patient's body. The method helps avoid significant arcing while allowing use of an energy delivery device or in words a medical device 10 in the vicinity of an electrically conductive object 50 such as a metallic object. In one particular example, the metallic object is a stent 52, as shown, that may have previously been placed within the vasculature to treat a condition within the body, for example such as an aneurismal vessel wall or at the site of a stenosis. Embodiments of the present method allow for an energy delivery parameter to be monitored during the delivery of energy from the medical device 10. The value of the energy delivery parameter is compared to a threshold value to determine if the value exceeds or falls below the threshold to ascertain if the medical device 10 is in proximity to the electrically conductive object 50. Additionally, the values obtained for the energy delivery parameter may be used to determine the relative distance between the medical device 10 and the electrically conductive object 50. The orientation of the medical device 10 may be adjusted and the energy delivery may then be controlled based on the relative proximity or distance determined between the medical device 10 and the electrically conductive object 50 such as the metal stent 52.

In some embodiments of the present invention, the energy delivery parameter may be current and the distance may calculated as a function of the electrical current that is detected. As illustrated in FIG. 6a, if a low value of current is detected then the medical device 10, and more specifically the energy delivery portion 12 of the medical device 10 such as device electrode 14, is determined to be relatively far from the electrically conductive object 50, as shown in FIG. 6a. In one such example, a baseline current value may be obtained as the medical device 10 is being advanced into the patient's body and a current may be measured as the medical device 10 (and specifically the device electrode 14) is closer to the electrically conductive object 50. If a low value of current is detected relative to baseline value then the medical device 10 [and the device electrode 14] is determined to be relatively far from the metallic object. On the contrary, in some examples, if a higher electrical current value is obtained then the device electrode 14 is determined to be closer to the metallic object. Still alternatively, if the current value exceeds a predetermined metal contact threshold that is indicative of metal contact error, the device electrode 14 is determined to be in contact with the metallic object. In some such embodiments, the values or characteristics of the energy delivery parameter may be mapped to physical distances in a physiologically relevant model. As such, some embodiments of the present invention provide a means to detect proximity by providing relative distance information between the medical device 10 and the electrically conductive object 50.

As such some embodiments of the present invention provide an indication to the user as to the relative distance the medical device 10 is away from the electrically conductive object 50 such as a metallic object during the course of the procedure. In accordance with an embodiment of the present invention, a method is provided that provides earlier detection of the metallic object as the medical device 10 is approaching it. More specifically, the method provides information relating to the relative distance between the medical device 10 and the metallic object as the device 10 is being advanced, which may allow the physician to alter or correct the course or trajectory of the medical device 10 in order to avoid the metallic object and/or deliver energy at a distance from the metallic object. Furthermore, it may allow the user to continue delivering energy while substantially avoiding contact with the metallic object.

In accordance with some embodiments of the present invention, a method is provided that provides for monitoring an energy delivery parameter of the device 10, where the energy delivery parameter that is impacted by the relative distance between the device 10 and the metallic object. This allows changes in the value of the energy delivery parameter to be used to provide an indication of the relative proximity of the device 10 to the metallic object. As the value of the energy delivery parameter changes, it is translated into a corresponding distance measurement/information to provide the user with an indication of the relative distance between the device 10 and the metallic object. Information about the proximity of the device 10 to the metallic object and the correction of the device trajectory prior to contact of the device with the metallic object, may allow for greater opportunity for course correction to avoid contact with the metallic object while continuing with the delivery of energy. This may allow for enhanced procedural efficiency and/or success. As such, some embodiments of the present invention may provide relative distance information between the device 10 and the metallic object and may provide an enhanced method to detect proximity that may involve the use of one or more energy thresholds to assess an energy delivery parameter.

Figure 6B:
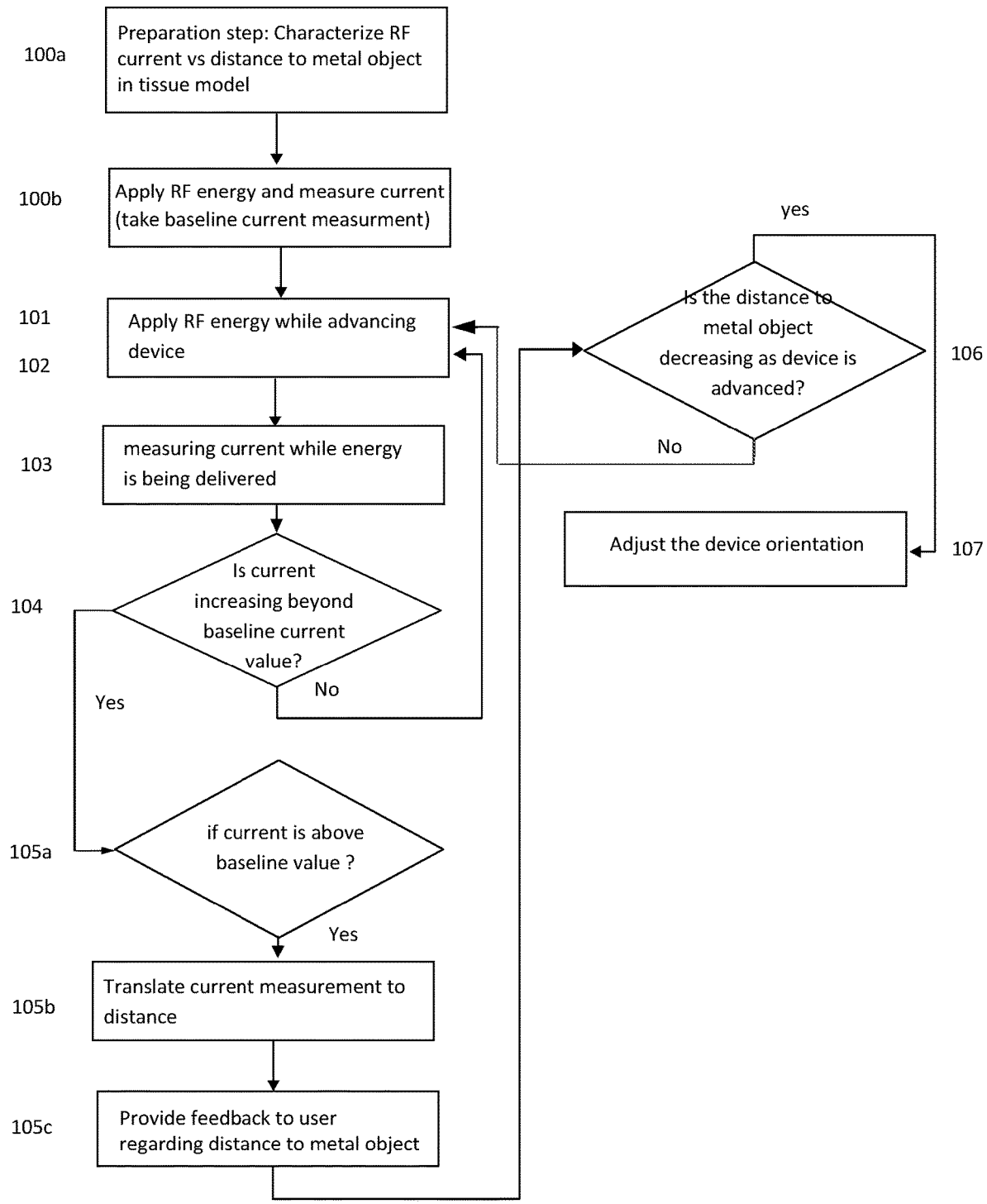
FIG. 6b is an illustration of a flowchart showing a method in accordance with an embodiment of the present invention.

More specifically, some embodiments of the present invention provide a means for providing an indication of the proximity between a device and a metallic object without requiring contact of the device with the metallic object allowing the physician to avoid contact with the metallic object through course correction. In one specific example, as shown in FIGS. 6b and 6c, a method is disclosed for delivering energy within a region of tissue within a patient's body using a medical treatment system, where the method provides for assessing proximity between the medical device 10 and the electrically conductive object 50 such as metallic object, for example a stent 52. The medical treatment system comprises a medical device 10 coupled to an energy delivery source. A general method of the present invention comprises the steps of (1) delivering energy from the medical device; (2) advancing the medical device to a target site within the patient's body; (3) measuring an energy delivery parameter while energy is being delivered; (4) detecting if [a value of] the energy delivery parameter crosses a threshold; (5) if the threshold is crossed thereby indicating proximity of the device to a conductive object, determining the relative distance between medical device and the conductive object based on [the detected values of] the energy delivery parameter; (6) determining if the distance between the medical device and metal object is decreasing; and (7) upon determining that the distance between the medical device and the conductive object is decreasing, adjusting a position of the medical device and repeating steps (3)-(7) until the medical device is positioned at a desired distance from the conductive object.

More specifically, in some embodiments as shown in FIGS. 6b and 7a-7d, the energy delivery parameter is current. In some examples, the RF current may be characterized and mapped to distance between the medical device 10 and electrically conductive object 50 (such as a stent 52), as shown at step 100a and as further illustrated in FIG. 8. In one such example, there may be a substantially linear relationship between current and distance values. In other examples there may be a slightly exponential relationship between current detected and the distance the medical device 10 is from the electrically conductive object 50. In some such examples, an initial current value may be obtained as the medical device 10 is initially advanced into the patient's body, as shown at step 100b in FIG. 6a, to function as an initial base value or baseline current value. This may also be used to confirm that the medical device 10 is not near a metallic object. This is further illustrated in FIG. 7a. The baseline value represents a relatively low electrical current value, which is recorded when the medical device 10 is outside the field of effect 54 of the electrically conductive object 50. For example, when the device electrode or energy delivery portion 12 is outside the field of effect of the electrically conductive object 50 e.g. metallic object (several centimeters), there is no increase in current and this is the baseline current value.

The method then comprises delivering energy as the medical device is advanced into the patient's body as shown by steps 101 and 102, respectively in FIG. 6b. The current values are then measured while energy is being delivered at step 103. These measurements may, in some embodiments, be repeated substantially continuously as the device is being advanced. The next step involves checking if the current is increasing beyond a threshold value at step 104 and detecting if a value of the current crosses the threshold. If at step 105a, the threshold is crossed, it indicates proximity of the device to an electrically conductive object. This is further illustrated in FIG. 7b, as the medical device 10 and such the device electrode 12 enters the field of effect 54 of the electrically conductive object, the value of the measured current is above the baseline threshold value.

In some examples, as noted above, the threshold value is equal to the base value or the baseline value which is measure or calculated at the beginning of the procedure, upon advancing the medical device to the target site within the patient's body. In other examples the threshold value may be equal to a pre-determined value of the energy delivery parameter, for example current. In some examples the threshold value may be equal to less than about 1.0 Amps. In some examples, the threshold value ranges from about 0.3 Amps to about 1.0 Amps. In a specific example, the threshold value is equal to about 0.3 Amps.

Figure 7A:
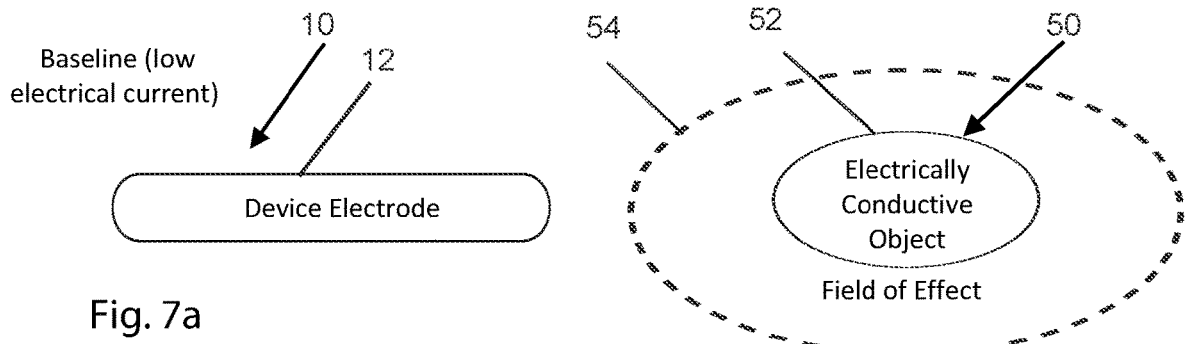
FIGS. 7a-7d are an illustration of a method in accordance with an embodiment of the present invention.
Figure 7B:
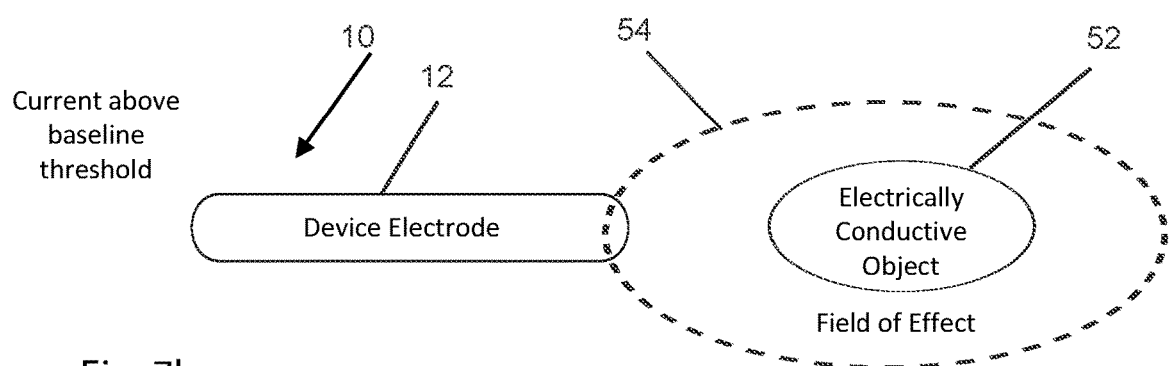
Figure 7C:
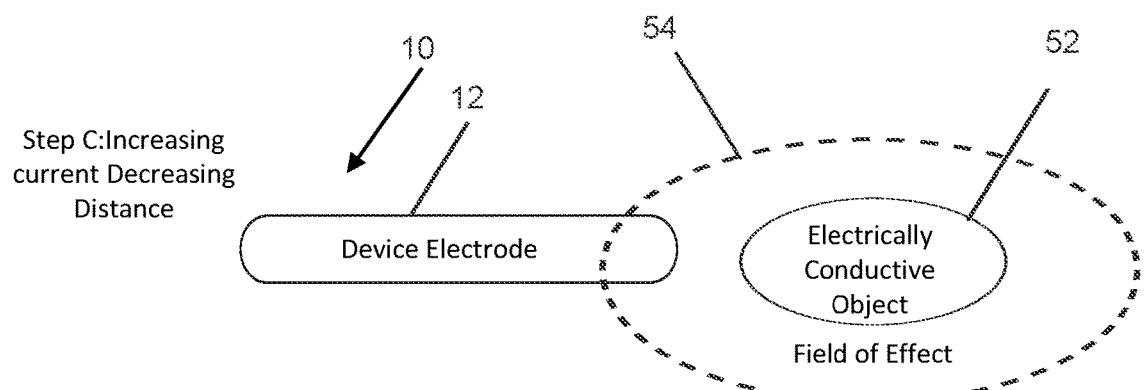
Figure 8:
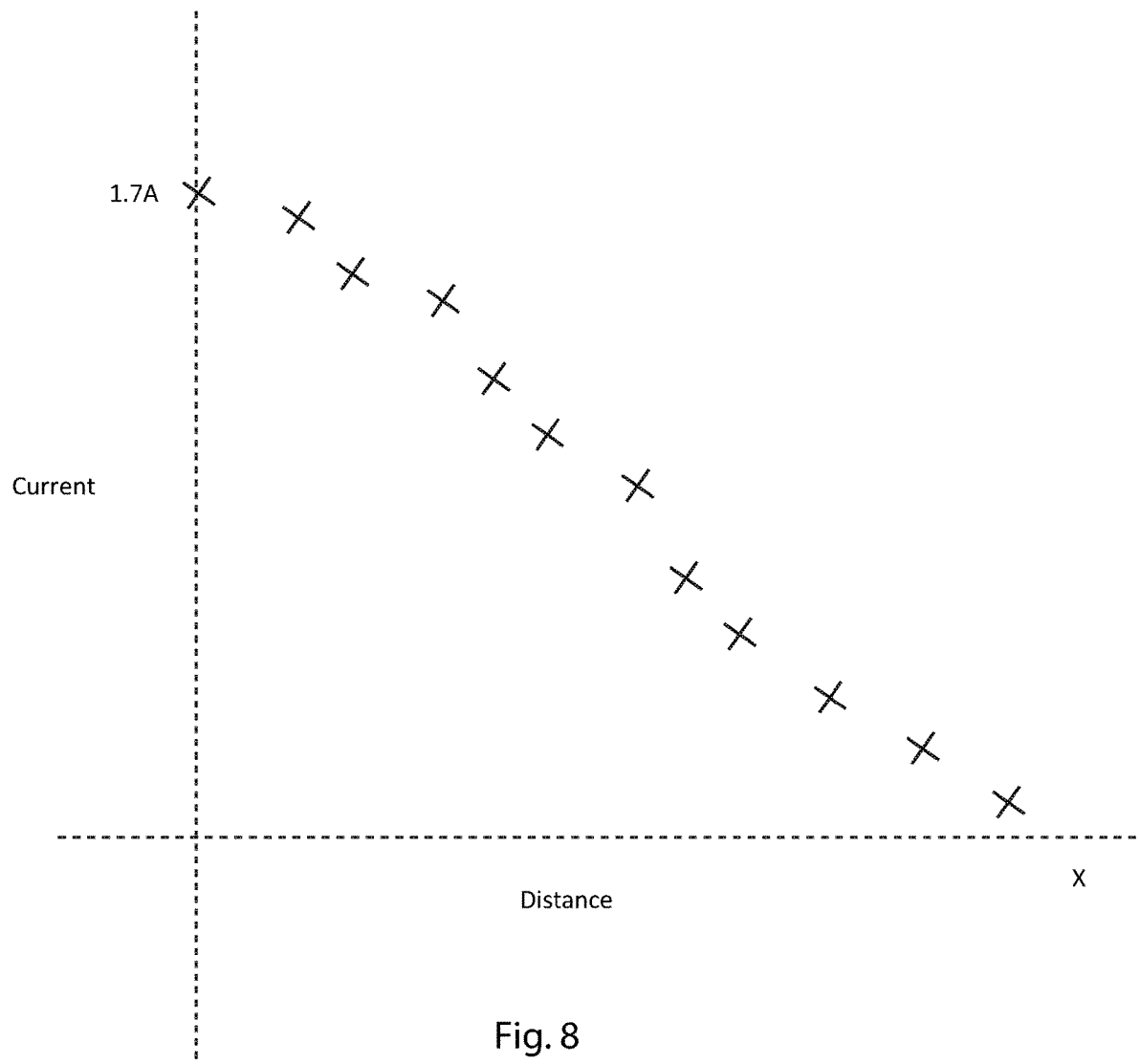
FIG. 8 is an illustration of mapping between current and distance in accordance with an embodiment of a method of the present invention.

In accordance with an embodiment of the present invention, once the measured value of current is detected to be greater than the baseline threshold value, the method then involves determining the relative distance between medical device 10 and the conductive object 50 based on the detected values of current at step 105b. In some examples, as shown in FIG. 6b, at step 105c feedback may be provided to the user about the distance values that are obtained. In some embodiments a method of the invention provides feedback that indicates to the user the relative distance between the medical device 10 and the conductive object. At step 106 it is then determined if the distance between the medical device and metal object is decreasing as the device is being advanced. This determination is made by comparing the distance measurements determined as the device is being advanced. As illustrated in FIG. 7c, as the device 10 is advanced further, the device electrode 12 enters further within the field of effect 54 of the electrically conductive object 52. As the distance between the device electrode or energy delivery portion 12 and the electrically conductively object 50 decreases, the values of the measured current increase. Based on the values of current obtained, if it is determined that the distance between the medical device and the conductive object is decreasing, the method of the present invention provides for adjusting a position of the medical device and repeating steps 103 to 107 until the medical device is positioned at a desired distance from the electrically conductive object 50. In some such examples, the medical device may encounter areas of radial boundaries/circles or contour profiles as it enters the field of effect 54 of the electrically conductive object. The radial boundaries represent a particular value for an energy delivery parameter such as current. The radial boundaries are equidistant from the electrically conductive object 50 and are at the same value of an energy delivery parameter. For example, the radial boundaries represent areas that are equipotential in the case the energy delivery parameter is voltage. Alternatively, the radial boundaries may represent areas that are equicurrent, or in other words they may represent areas where the detected current has the same value.

In some embodiments, the method of the present invention may additionally be used to provide feedback/indicate to the user, if the distance between the medical device and the conductive object is increasing or decreasing. In some examples the indication may be provided at any one of steps 105a to 107, shown in FIG. 6b. In a specific example, indication/feedback is provided to the user if the distance between the medical device and metal object is determined to be decreasing. In some examples, the step of providing an indication/feedback to the user comprises providing a visual indication. Alternatively, the step of providing an indication/feedback to the user comprises providing an electrical control signal. Still furthermore, the step of providing an indication/feedback to the user comprises providing an acoustic indication. In some such examples, the acoustic indication is taken from the group consisting of a volume based acoustic indication and a frequency based acoustic indication. In some embodiments, if the electrical current is greater than about 1.7 Amps, it indicates direct metal contact. In some examples, if the electrical current values range from between about 1.0 Amps to about 2.0 Amps, they are indicative of direct metal contact. In other examples, if the electrical current values are greater than about 2.0 Amps, they are indicative of direct metal contact. Still in other examples, if the electrical current is equal to about 1.7 Amps, it provides an indication of direct metal contact.

Figure 7D:
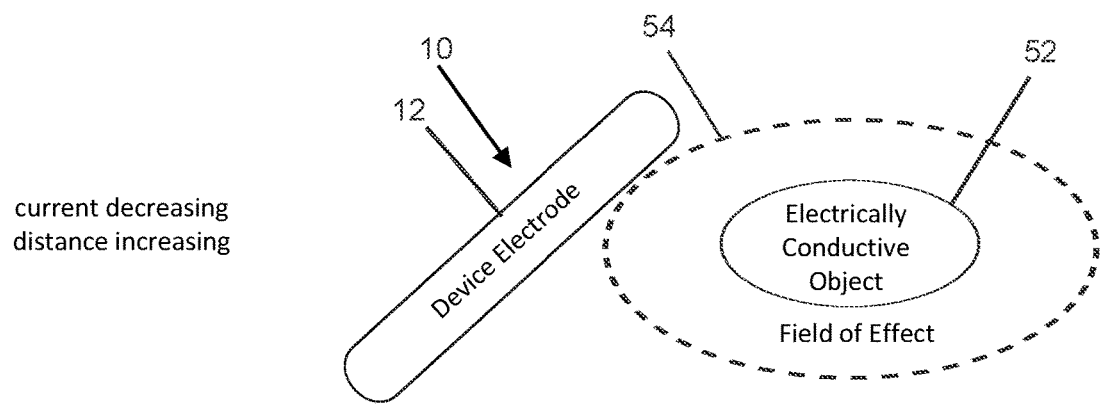

In some embodiments, at step 107, the step of adjusting a position of the medical device 10 comprises directing the device away from the metallic object as shown in FIG. 7d. As the device moves away from the field of effect 54 of the electrically conductive object the current decreases which is indicative of the distance increasing between the device electrode or energy delivery portion 12 and the electrically conductive object 50. This in some embodiments it may be desirable to provide proximity information to the user so the user can avoid contact with the electrically conductive object 50 such as a metallic object. For example if a metallic object is a stent 52 which has been previously placed within a vasculature within the patient's body to treat a medical condition. Then it is desirable to provide information to the physician of the medical device 10 is approaching the stent 52 and to provide an indication to the physician if the medical device is too close to the stent 52. In one such example, the step of adjusting a position of the medical device (step 107) comprises moving the medical device 10 away from the conductive object 50 until measurement no longer exceeds the threshold. As such in some embodiments, a method of the present invention provides a negative feedback mechanism to prevent a medical device 10 from contacting an electrically conductive object while still allowing the medical device to deliver energy.

In an alternative embodiment, it may be desirable to provide the physician feedback in procedures where it may be desirable to guide the medical device 10 towards the conductive object 50. In one such example the conductive object 50 may function as a guide or marker to facilitate advancement of the medical device 10 towards a target site. In one such example, the electrically conductive object 50 comprises a secondary medical device and the step of adjusting a position of the medical device in accordance with the method of the present invention, comprises moving the medical device towards the secondary medical device. In such example, a method of the present invention facilitates advancement of the medical device 10 through the liver parenchyma from a hepatic vein to the portal vein in order to assist with a trans-jugular portosystemic hepatic shunt (TIPS) procedure for example as described in more detail in U.S. provisional application No. 62/208,404, filed on Aug. 21, 2015 and U.S. provisional application No. 62/208,138, filed on Aug. 21, 2015. These application are hereby incorporated by reference in their entirety. In such embodiments, the secondary medical device may comprise a medical guidewire or a snare that is positioned within a portal vein. The method allows for adjusting the position of the medical device until it is positioned adjacent the secondary medical device. Thus, in some embodiments of the present invention, the method of the present invention provides a positive feedback mechanism to allow a medical device 10 to be directed towards the electrically conductive object 50 which may be a secondary medical device. An additional example of a method where it is desirable to direct a medical device towards a secondary medical device such as a snare or a guidewire is disclosed in U.S. application Ser. No. 13/912,244 filed on Jun. 7, 2013, which is also hereby incorporated by reference in its entirety. This application discloses further details of a method of traversing an occlusion where a medical device is directed towards a secondary medical device that is positioned on an opposite side of the occlusion and that functions as a target to guide the medical device.

As such, some embodiments of the present invention enable the user to navigate a medical device to either avoid or approach an electrically conductive object 50 such as a metallic object. Some embodiments, as described previously provide for a step of determining if the distance between the medical device and metal object is decreasing. Alternatively, some embodiments may provide for a step of determining if the distance between the medical device and metal object is increasing. If it is desired to avoid a target the user may then continue on the path the device is travelling in. If it is desired that the medical device is advanced towards the electrically conductive object which may be functioning as a target, then the method comprises adjusting an orientation of the device to direct the device towards the electrically conductive object.

In some examples described herein above, the step of adjusting a position of the medical device 10 is performed automatically. In a specific example, the step of adjusting a position of the medical device 10 is performed automatically using an automated navigation system. One such method comprises a step of additionally providing an indication/feedback to the user through an electrical control signal that is receivable by the automated navigation system.

In another example the step of adjusting a position of the medical device 10 is performed concurrently with a step of imaging the medical device. For example, the step of imaging the medical device 10 may be performed using an imaging modality taken from the group consisting of: fluoroscopy, magnetic resonance imaging, computerized tomography scan, electro-anatomical mapping and magnetic positioning system. It may also be helpful to image the medical device 10 concurrently with the steps of advancing the medical device 10 and measuring the base value of current. Still furthermore, any of the steps 100-107 of a method of the present invention may be performed concurrently with a step of imaging the medical device 10. In some examples, a method of imaging may be of the type described in U.S. provisional application No. 62/208,138, filed on Aug. 21, 2015 which is hereby incorporated by reference in its entirety.

In accordance with various embodiments of the present invention, the energy delivery parameter may be selected from the group consisting of: current, voltage, phase, frequency and impedance.

As such some embodiments of the present invention as described herein above provide a method and means to provide metal proximity information without requiring direct contact with a metallic object (e.g. a stent) before triggering an error or indication. While contact with a metallic object may also provide useful information to the physician, providing information or knowledge that the medical device is approaching the metallic object may allow contact to be avoided altogether through course correction. Furthermore, providing this additional feedback to the operator may result in greater procedural success. By monitoring an energy delivery parameter such current amplitude, voltage amplitude and phase of a radiofrequency (RF) signal, it is possible to determine the relative distance between the device and an electrically conductive object such as a metallic object. As such embodiments of the present invention provide a method that provides the ability to characterize and monitor electrical energy delivery properties or parameters such as current, voltage, phase and frequency and further provides mapping of these characteristics to physical distances in a physiologically relevant model. Some examples of the present embodiment provide relative distance information and have the ability to provide relative distance information using one or more thresholds (which may in some cases be fixed thresholds).

In some examples, a method of the present invention may be used in interventional procedures near metal objects, where it is preferable to avoid contact with these objects altogether. In specific cases involving stents that have previously been placed to treat chronic total occlusions (CTOs), a medical device may be required to be advanced through the stent. In such cases where the device is inside a stent (which outlines the vessel wall), it may be desirable to stay as close to the central lumen of the vessel as possible, in order to avoid unintentionally exiting the vessel wall (into the extravascular space). The method allows for monitoring gradual changes in electrical signal characteristics or values of the energy delivery that correspond with the distance to the electrically conductive objects. In some examples as outlined previously, the present invention monitors the amplitude (instantaneous value and change) in current of the RF signal, in order to determine the relative distance between the device and the electrically conductive object, such as a metallic object. The present invention can also be used to avoid contact with metallic objects during minimally invasive interventional medical procedures. It can additionally guide a physician on how the device orientation needs to be altered in order to stay on-course to advance through a vessel lumen (for example in a case where the device electrode is inside a stent that outlines the vessel wall).

In some embodiments, an invention of the present invention provides the ability to characterize and monitor the electrical signal properties (e.g. current, voltage, phase, frequency). It additionally allows for mapping of distance between the device and the electrically conductive object such as a metallic object vs. a signal property (such as an electrical signal property such as current amplitude). As outlined previously, in one particular example, electrical current greater than about 1.7 Amps indicates direct metal contact. Whereas, when the device electrode is outside field of effect of the metallic object (several centimeters), there is no increase in current—forming the baseline current value. Then as the device electrode gets closer to the metallic object, the electrical current will increase until the point of contact. The distance between the medical device and the metallic object can be determined by assessing the current values and as noted above, feedback can be provided to the physician regarding the distance between the medical device and the metallic object. This can be a visual indicator such as scale bar, acoustic indicator (such as a volume feedback or sound frequency). The orientation of the medical device may be adjusted based on the feedback. As described previously, some embodiments of the invention require an electrosurgical device, RF energy source with current measuring ability, presence of an electrically conductive object such as a metallic object within the body which may be in the proximity of the electrosurgical device electrode during use and a feedback mechanism to provide feedback/indication to the physician. A specific example of such a method of the present invention has been described previously as shown in FIG. 6b.

In accordance with some alternatives of the present invention, an alternative to measuring current amplitude, voltage, phase, frequency or impedance may be monitored and measured. In some examples physician navigation may be used to reorient the device. Alternatively, automated navigation system (e.g. a surgical robotic system) may be used to reorient and/or adjust the position of the device. In some examples, a fluoroscopy based imaging or navigational modality may be used to assist with the procedure. Alternatively, other imaging or navigational modalities may be used such as MRI, CT, electro-anatomical mapping, magnetic positioning system (GPS for OR). In some examples as noted previously, the electrically conductive object may be a metallic object within the body. Alternatively, in addition to an electrically conductive object, a method embodiment of the present invention may be usable with a highly conductive medium. The method may be used to avoid certain tissues or cavities in the body (e.g. cerebrospinal fluid which may be quite electrically conductive). One example of an imaging method may be used as described in In some examples, a method of imaging may be of the type described in U.S. provisional application No. 62/208,138, filed on Aug. 21, 2015 which is hereby incorporated by reference in its entirety.

As still a further alternative of the present invention, a 3D imaging modality may be used to image device and metallic object. (E.g. CT or potentially MRI). These may be used in an interventional procedure. Alternatively, a method of the present invention may involve, placing multiple neutral electrodes (grounding pads on the body and measuring the current/impedance from the device to each of these locations. This data may be used to provide triangulation methods to determine the relative position of the metallic object which may include a value representing distance as well as direction.

Figure 9:
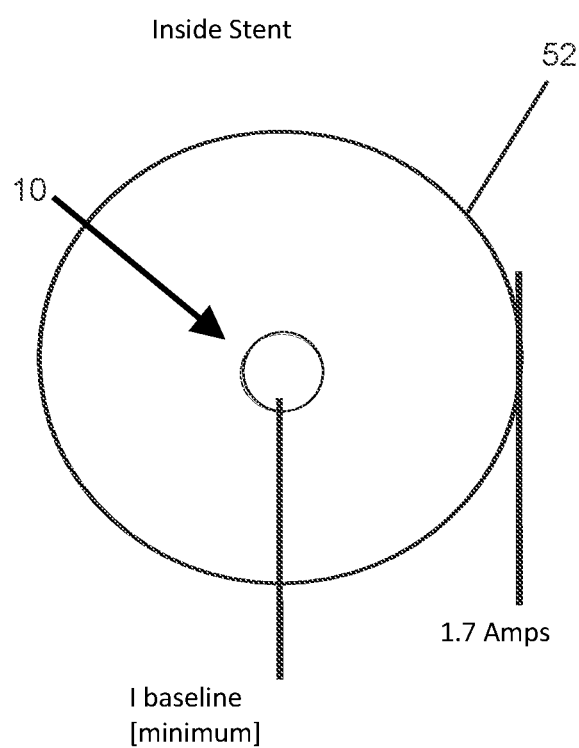
FIG. 9 is an illustration of a stent and a medical device as well as relative current values with respect to distance, in accordance with an embodiment of a method of the present invention.

In one specific example, in accordance with a method of the present invention, a medical device may be advanced in a straight line towards the electrically object. A one dimensional view may be obtained of the device travelling in a straight line towards the electrically conductive object. Based on location of medical device relative to the tissue and electrically conductive object a nominal value may be obtained. In one particular case, the medical device may be advanced through the center of an electrically conductive object such as a stent, where the baseline measurement may represent a measurement taken along the linear path along the center of the stent. In some examples, the distance between the metallic outer wall of the stent and the center location of the medical device may be mapped as a linear relationship in a tissue model. As the medical device deviates from the center trajectory towards the exterior wall of the stent the values of the current detected goes up from the nominal or baseline value where a current value of greater than about 1.7 Amps represents contact of the medical device with an exterior wall of the stent, as shown in FIG. 9. The relationship between current and distance may be a linear relationship as the medical device moves radially towards the exterior of the stent. An indication may be provided to the user as the detected value of current goes up to indicate to the user that the medical device is moving radially towards the exterior of the stent. The indication additionally functions to indicate to the user to move the medical device back to the original relatively central position (within the stent). In some embodiments, the baseline value is about 0.3 Amps and may represent the minimum baseline current value. The value of the baseline current may be obtained with or without imaging and may function as an absolute reference value.

In some such embodiments, a step of imaging may be used in conjunction with measuring and monitoring current to ensure that the medical device remains at the nominal baseline value to ensure the device trajectory is through substantially a center of stent. In one example, the imaging modality may be fluoroscopy and two images may be obtained to ensure that the medical device remains substantially in a center of the cross-section defined by the stent. In one particular case, the two images are taken perpendicular to the plane of view [e.g. a bi-planar approach]. In one example, the two perpendicular view may be an A-P view and a lateral view. Alternatively, the two views may be two versions of oblique views, the Right Anterior Oblique (RAO) and the corresponding perpendicular view which is the Left Anterior Oblique (LAO). Once the views are obtained, the method involves for checking for deviation of the medical device with respect to the center trajectory. Alternatively, CT or MRI cross-sectional views may be obtained—various slices may be captured for an MRI view. Then using the initial view of the medical device travelling through the center of the stent, if the device is found to be getting close to the stent wall (for example from the current values obtain), then cross-sectional views and/or imaging slices obtained through subsequent imaging may be used to find out if the medical device is getting close to the stent edge or periphery. This may supplement the information that is obtained through changes in current such as increased values of current that may be observed. Then a position of the medical device may be adjusted to move the medical device trajectory such that is through the center of the stent. In some cases a stent of imaging such as fluoroscopy, MRI or CT may be used to assist with reposition or reorienting of the medical device.

In accordance with a broad aspect embodiments of the present invention comprise a method is disclosed for delivering energy within a region of tissue within a patient's body using a medical treatment system, the medical treatment system comprising a medical device coupled to an energy delivery source, the method comprising the steps of: (1) delivering energy from the medical device; (2) advancing the medical device to a target site within the patient's body; (3) measuring an energy delivery parameter while energy is being delivered; (4) detecting if [a value of] the energy delivery parameter crosses a threshold; (5) if the threshold is crossed thereby indicating proximity of the device to a conductive object, determining the relative distance between medical device and the conductive object based on [the detected values of] the energy delivery parameter; (6) determining if the distance between the medical device and metal object is decreasing; and (7) upon determining that the distance between the medical device and the conductive object is decreasing, adjusting a position of the medical device and repeating steps (3)-(7) until the medical device is positioned at a desired distance from the conductive object.

In accordance with an additional broad aspect, embodiments of the present invention comprise a method for delivering energy within a region of tissue within a patient's body using a medical treatment system, the medical treatment system comprising a medical device coupled to an energy delivery source, the method comprising: (1) delivering energy from a medical device to material within a patient's body; (2) measuring an energy delivery parameter while the energy is being delivered; (3) detecting [an error if one or more values of] the energy delivery parameter crosses a threshold; (4) if the threshold is crossed, determining whether the medical device is sufficiently distanced from a conductive object to allow for safe delivery of energy to the patient's body, by assessing an extent [of the error/by which the one or more values of] the energy delivery parameter that cross the threshold; and (5) if the medical device is determined to not be sufficiently distanced from the conductive object, adjusting a position of the medical device and repeating steps (2)-(4) until the medical device is sufficiently distanced from the conductive object.

In accordance with still an additional broad aspect, embodiments of the present invention comprise a method for delivering energy within a region of tissue within a patient's body using a medical treatment system, the medical treatment system comprising a medical device coupled to an energy delivery source, the method comprising the steps of: (1) delivering energy from the medical device to a material within a patient's body; (2) measuring return current while energy is being delivered; (3) detecting [one or more over-currents] if the return current exceeds a threshold; (4) if the threshold is exceeded, assessing the extent [of the one or more over-currents] by which the return current exceeds the threshold to determine if the medical device is sufficiently distanced from a conductive object; and (5) if the medical device is determined to not be sufficiently distanced from the conductive object, adjusting a position of the medical device and repeating steps (2)-(4) until the medical device is sufficiently distanced from the conductive object.

Thus, as described herein, in accordance with various embodiments, a method is disclosed for delivering energy within a region of tissue within a patient's body. The method helps avoid significant arcing while allowing use of an energy delivery device in the vicinity of an electrically conductive object such as a metallic object. An energy delivery parameter is monitored during the delivery of energy. The value of the energy delivery parameter is compared to a predetermined magnitude threshold to determine if the value exceeds or falls below the predetermined threshold to ascertain if there is significant arcing. The energy delivery is then controlled based on the extent of the arcing observed.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method for delivering energy to a region of tissue within a patient's body using a medical treatment system, the medical treatment system comprising an energy delivery device coupled to an energy delivery source, the method comprising the steps of:
   (1) delivering energy through said energy delivery device;
   (2) monitoring an energy delivery parameter associated with the delivery of energy by the medical treatment system;
   (3) detecting one or more errors if one or more values of the energy delivery parameter exceed a predetermined magnitude threshold;
   (4) determining an extent of the errors detected; and
   (5) controlling the delivery of energy if the extent of the errors detected exceeds a sensitivity threshold over a predetermined time period.

2. The method of claim 1, wherein the step of determining the extent of the errors comprises a step of determining the number of errors detected.

3. The method of claim 1, wherein the step of determining the extent of the errors comprises a step of determining the duration of time during which the one or more errors are detected.

4. The method of claim 3, wherein the energy delivery parameter is selected from the group consisting of: current, voltage, impedance and power.

5. The method of claim 1, wherein the energy delivery device is selected from the group consisting of an RF (radiofrequency) cutting device and an RF (radiofrequency) ablation device.

6. The method of claim 1, wherein the energy delivery parameter is current.

7. The method of claim 6, wherein the threshold is between about 0.3 Amps to about 1.0 Amps.

8. A method for delivering energy to a region of tissue within a patient's body using a medical treatment system, the medical treatment system comprising a medical device coupled to an energy delivery source, the method comprising:
   (1) delivering energy from a medical device to material within a patient's body;
   (2) measuring an energy delivery parameter while the energy is being delivered;
   (3) detecting at least one error if one or more values of the energy delivery parameter cross a pre-determined threshold;
   (4) upon detection of at least one error, assessing an extent of the at least one error to determine whether the medical device is sufficiently distanced from a conductive object to allow for safe delivery of the energy to the material within the patient's body; and
   (5) if the medical device is determined to not be sufficiently distanced from the conductive object, adjusting a position of the medical device and repeating steps (2)-(4) until the medical device is sufficiently distanced from the conductive object.

9. The method of claim 8, wherein the energy delivery parameter is selected from the group consisting of: current, voltage, phase, frequency and impedance.

10. The method of claim 8, wherein the step of assessing an extent of the at least one error comprises quantifying a number of times the energy delivery parameter crosses the threshold.

11. The method of claim 8, wherein the step of assessing an extent of the at least one error comprises determining if a collective magnitude of the one or more values of the energy delivery parameter exceeds a sensitivity threshold over a predetermined time period.

12. The method of claim 11, wherein the sensitivity threshold is fixed.

13. The method of claim 12, wherein the sensitivity threshold is adjustable.

14. The method of claim 8 wherein the step of assessing an extent of the at least one error comprises determining a duration of time over which the energy delivery parameter exceeds the threshold.

15. The method of claim 8, wherein the medical device is selected from the group consisting of a radiofrequency cutting device and a radiofrequency ablation device.

16. A method for delivering energy to a region of tissue within a patient's body using a medical treatment system, the medical treatment system comprising a medical device coupled to an energy delivery source, the method comprising the steps of:
(1) delivering energy from the medical device to a material within a patient's body;
(2) measuring a return current while the energy is being delivered;
(3) detecting if the return current exceeds a threshold;
(4) if the threshold is exceeded, assessing an extent by which the return current exceeds the threshold to determine if the medical device is sufficiently distanced from a conductive object; and
(5) if the medical device is determined to not be sufficiently distanced from the conductive object, adjusting a position of the medical device and repeating steps (2)-(4) until the medical device is sufficiently distanced from the conductive object.

17. The method of claim 16, wherein the threshold is equal to a base value, and wherein the method further comprises a step of determining a base value by measuring the current upon advancing the medical device to a target site within the patient's body.

18. The method of claim 17, further comprising a step of imaging the medical device, wherein the steps of advancing the medical device and measuring the base value are performed concurrently with the step of imaging the medical device.

19. The method of claim 16, further comprising a step of imaging the medical device, wherein the step of adjusting the position of the medical device is performed concurrently with the step of imaging the medical device.

20. The method of claim 18, wherein the step of imaging the medical device is performed using an imaging modality selected from the group consisting of: fluoroscopy, magnetic resonance imaging, computerized tomography scan, electro-anatomical mapping and magnetic positioning system.

21. The method of claim 19, wherein the step of imaging the medical device is performed using an imaging modality selected from the group consisting of: fluoroscopy, magnetic resonance imaging, a magnetic positioning system.

22. The method of claim 16, further comprising a step of providing a feedback to a user if the distance between the medical device and the conductive object is determined to be decreasing.

23. The method of claim 22, wherein the feedback is selected from the group consisting of a visual indication, an electrical control signal and an acoustic indication.

24. The method of claim 23, wherein the acoustic indication is selected from the group consisting of a volume based acoustic indication and a frequency based acoustic indication.

25. The method of claim 16, wherein the step of adjusting the position of the medical device is performed automatically.

26. The method of claim 25, wherein the step of adjusting a position of the medical device is performed using an automated navigation system.

27. The method of claim 22, wherein the step of adjusting a position of the medical device is performed automatically using an automated navigation system, and wherein the step of providing feedback to the user comprises providing an electrical control signal that is receivable by the automated navigation system.

* * * * *